(12) United States Patent
    Albert

(10) Patent No.: US 8,700,137 B2
(45) Date of Patent: Apr. 15, 2014

(54) CARDIAC PERFORMANCE MONITORING SYSTEM FOR USE WITH MOBILE COMMUNICATIONS DEVICES

(71) Applicant: AliveCor, Inc., San Francisco, CA (US)

(72) Inventor: David E. Albert, Oklahoma City, OK (US)

(73) Assignee: AliveCor, Inc., San Francisco, CA (US)

( * ) Notice: Subject to any disclaimer, the term of this patent is extended or adjusted under 35 U.S.C. 154(b) by 0 days.

(21) Appl. No.: 14/015,303

(22) Filed: Aug. 30, 2013

(65) Prior Publication Data

US 2014/0066798 A1    Mar. 6, 2014

Related U.S. Application Data

(60) Provisional application No. 61/695,278, filed on Aug. 30, 2012.

(51) Int. Cl.
    *A61B 5/04*    (2006.01)
(52) U.S. Cl.
    USPC .......................................... 600/513; 600/514
(58) Field of Classification Search
    USPC .................................................. 600/513–514
    See application file for complete search history.

(56) References Cited

U.S. PATENT DOCUMENTS

| | | |
|---|---|---|
| 3,717,857 A | 2/1973 | Evans |
| 3,731,311 A | 5/1973 | Williams |
| 3,768,014 A | 10/1973 | Smith et al. |
| 3,779,237 A | 12/1973 | Goeltz et al. |
| 3,782,367 A | 1/1974 | Hochberg et al. |
| 3,805,227 A | 4/1974 | Lester |
| 3,882,277 A | 5/1975 | DePedro et al. |
| 3,885,552 A | 5/1975 | Kennedy |
| 3,898,984 A | 8/1975 | Mandel et al. |
| 3,909,599 A | 9/1975 | Trott, Jr. et al. |
| 4,027,146 A | 5/1977 | Gilmore |

(Continued)

FOREIGN PATENT DOCUMENTS

| | | |
|---|---|---|
| CH | 675675 A5 | 10/1990 |
| CN | 201918016 U | 8/2011 |

(Continued)

OTHER PUBLICATIONS

Adidas miCoach Pacer Review: Like Nike+, Only Better; printed from website http://gizmodo.com/5479456/adidas on Mar. 4, 2010; 5 pgs.

(Continued)

*Primary Examiner* — Nicole F Lavert
(74) *Attorney, Agent, or Firm* — Shay Glenn LLP

(57) ABSTRACT

Described herein are apparatuses (e.g., devices, systems, software), and methods for monitoring the cardiac health of a patient. The apparatuses and methods may include a smartphone or hand held computing device having an accelerometer. The apparatus may also include a device with a plurality of electrodes integral with or attached to the smartphone. The devices can be placed on a patient's chest to measure electrical signals and vibrations on the chest caused by the heartbeat. The measurements can generate a seismocardiogram (SCG) and in some variations an electrocardiogram (ECG). The apparatuses and methods can analyze the data in the SCG to produce a measure of the cardiac function. Changes in such measures can provide an early warning for potential cardiac problems and signal the need for the patient to seek treatment prior to a fatal cardiac event.

26 Claims, 8 Drawing Sheets

(56) References Cited

U.S. PATENT DOCUMENTS

| | | |
|---|---|---|
| 4,045,767 A | 8/1977 | Nishihara et al. |
| 4,083,366 A | 4/1978 | Gombrich et al. |
| 4,095,050 A | 6/1978 | Beachem et al. |
| 4,231,031 A | 10/1980 | Crowther et al. |
| 4,250,888 A | 2/1981 | Grosskopf |
| 4,281,664 A | 8/1981 | Duggan |
| 4,318,130 A | 3/1982 | Heuer |
| 4,409,984 A | 10/1983 | Dick |
| 4,531,527 A | 7/1985 | Reinhold, Jr. et al. |
| 4,567,883 A | 2/1986 | Langer et al. |
| 4,580,250 A | 4/1986 | Kago et al. |
| 4,803,625 A | 2/1989 | Fu et al. |
| 4,938,229 A | 7/1990 | Bergelson et al. |
| 4,981,141 A | 1/1991 | Segalowitz |
| 5,023,906 A | 6/1991 | Novas |
| 5,136,555 A | 8/1992 | Gardos |
| 5,191,891 A | 3/1993 | Righter |
| 5,218,969 A | 6/1993 | Bredesen et al. |
| 5,301,679 A | 4/1994 | Taylor |
| 5,321,618 A | 6/1994 | Gessman |
| 5,333,616 A | 8/1994 | Mills et al. |
| 5,336,245 A | 8/1994 | Adams et al. |
| 5,337,752 A | 8/1994 | Reeves |
| 5,339,824 A | 8/1994 | Engira |
| 5,360,005 A | 11/1994 | Wilk |
| 5,365,935 A | 11/1994 | Righter et al. |
| 5,410,587 A | 4/1995 | Grunwell |
| 5,433,736 A | 7/1995 | Nilsson |
| 5,452,356 A | 9/1995 | Albert |
| 5,466,246 A | 11/1995 | Silvian |
| 5,481,255 A | 1/1996 | Albert et al. |
| 5,503,158 A | 4/1996 | Coppock et al. |
| 5,539,705 A | 7/1996 | Akerman et al. |
| 5,544,661 A | 8/1996 | Davis et al. |
| 5,551,953 A | 9/1996 | Lattin et al. |
| 5,561,712 A | 10/1996 | Nishihara |
| 5,568,448 A | 10/1996 | Tanigushi et al. |
| 5,579,284 A | 11/1996 | May |
| 5,608,723 A | 3/1997 | Felsenstein |
| 5,661,699 A | 8/1997 | Sutton |
| 5,675,325 A | 10/1997 | Taniguchi et al. |
| 5,735,285 A | 4/1998 | Albert et al. |
| 5,742,251 A | 4/1998 | Gerber |
| 5,764,763 A | 6/1998 | Jensen et al. |
| 5,825,718 A | 10/1998 | Ueki et al. |
| 5,844,997 A | 12/1998 | Murphy, Jr. |
| 5,861,018 A | 1/1999 | Feierbach |
| 5,889,730 A | 3/1999 | May |
| 5,970,388 A | 10/1999 | Will |
| 5,982,297 A | 11/1999 | Welle |
| 6,024,705 A | 2/2000 | Schlager et al. |
| 6,037,704 A | 3/2000 | Welle |
| 6,048,319 A | 4/2000 | Hudgins et al. |
| 6,236,889 B1 | 5/2001 | Soykan et al. |
| 6,264,614 B1 | 7/2001 | Albert et al. |
| 6,319,201 B1 | 11/2001 | Wilk |
| 6,343,049 B1 | 1/2002 | Toda |
| 6,363,139 B1 | 3/2002 | Zurek et al. |
| 6,377,843 B1 | 4/2002 | Naydenov et al. |
| 6,418,394 B1 | 7/2002 | Puolakanaho et al. |
| 6,433,689 B1 | 8/2002 | Hovind et al. |
| 6,453,164 B1 | 9/2002 | Fuller et al. |
| 6,507,734 B1 | 1/2003 | Berger et al. |
| 6,549,756 B1 | 4/2003 | Engstrom |
| 6,717,983 B1 | 4/2004 | Toda |
| 6,790,178 B1 | 9/2004 | Mault et al. |
| 6,820,057 B1 | 11/2004 | Loch et al. |
| 6,845,263 B2 | 1/2005 | Kawaguchi |
| 6,950,681 B2 | 9/2005 | Hofmann |
| 6,970,737 B1 | 11/2005 | Brodnick et al. |
| 7,018,339 B2 | 3/2006 | Birnbaum et al. |
| 7,031,745 B2 | 4/2006 | Shen |
| 7,061,381 B2 | 6/2006 | Forcier et al. |
| 7,107,095 B2 | 9/2006 | Manolas |
| 7,260,429 B2 | 8/2007 | Siejko et al. |
| 7,324,836 B2 | 1/2008 | Steenstra et al. |
| 7,351,207 B2 | 4/2008 | Priemer |
| 7,354,400 B2 | 4/2008 | Asafusa et al. |
| 7,383,297 B1 | 6/2008 | Atsmon et al. |
| 7,444,116 B2 | 10/2008 | Ivanov et al. |
| 7,520,860 B2 | 4/2009 | Guion-Johnson et al. |
| 7,542,878 B2 | 6/2009 | Nanikashvili |
| 7,548,623 B2 | 6/2009 | Manabe |
| 7,603,148 B2 | 10/2009 | Michalak |
| 7,654,148 B2 | 2/2010 | Tomlinson, Jr. et al. |
| 7,668,589 B2 | 2/2010 | Bauer |
| 7,701,895 B2 | 4/2010 | Gehasie et al. |
| 7,742,808 B2 | 6/2010 | Nissilä |
| 7,819,814 B2 | 10/2010 | Gavriely et al. |
| 7,945,064 B2 | 5/2011 | O'Brien, Jr. et al. |
| 7,955,273 B2 | 6/2011 | Rahe-Meyer |
| 8,019,609 B2 | 9/2011 | Tamir et al. |
| 8,062,090 B2 | 11/2011 | Atsmon et al. |
| 8,078,136 B2 | 12/2011 | Atsmon et al. |
| 8,078,278 B2 | 12/2011 | Penner |
| 8,126,566 B2 | 2/2012 | Stahmann et al. |
| 8,130,093 B2 | 3/2012 | Mazar et al. |
| 8,160,276 B2 | 4/2012 | Liao et al. |
| 8,165,677 B2 | 4/2012 | Von Arx et al. |
| 8,301,232 B2 | 10/2012 | Albert et al. |
| 8,509,882 B2 | 8/2013 | Albert et al. |
| 2001/0031998 A1 | 10/2001 | Nelson et al. |
| 2001/0051766 A1 | 12/2001 | Gazdzinski |
| 2002/0111556 A1 | 8/2002 | Wegner |
| 2003/0004425 A1 | 1/2003 | Narimatsu et al. |
| 2003/0093002 A1 | 5/2003 | Kuo |
| 2003/0117987 A1 | 6/2003 | Brebner |
| 2003/0193839 A1 | 10/2003 | Singh |
| 2004/0117212 A1* | 6/2004 | Kong et al. .................. 705/2 |
| 2004/0215088 A1 | 10/2004 | Hubelbank |
| 2004/0215094 A1 | 10/2004 | Baumer et al. |
| 2004/0220487 A1 | 11/2004 | Vyshedskiy et al. |
| 2004/0220488 A1 | 11/2004 | Vyshedskiy et al. |
| 2004/0236819 A1 | 11/2004 | Anati et al. |
| 2004/0266407 A1 | 12/2004 | Lee et al. |
| 2005/0014531 A1 | 1/2005 | Findikli |
| 2005/0078533 A1 | 4/2005 | Vyshedskiy et al. |
| 2006/0022833 A1 | 2/2006 | Ferguson et al. |
| 2006/0047215 A1 | 3/2006 | Newman et al. |
| 2006/0173259 A1 | 8/2006 | Flaherty et al. |
| 2006/0190045 A1 | 8/2006 | Marcus et al. |
| 2006/0252999 A1 | 11/2006 | Devaul et al. |
| 2007/0021677 A1 | 1/2007 | Markel |
| 2007/0027386 A1 | 2/2007 | Such et al. |
| 2007/0063850 A1 | 3/2007 | Devaul et al. |
| 2007/0106179 A1 | 5/2007 | Bagha et al. |
| 2007/0254604 A1 | 11/2007 | Kim |
| 2007/0265038 A1 | 11/2007 | Kim |
| 2008/0009759 A1 | 1/2008 | Chetham |
| 2008/0058670 A1 | 3/2008 | Mainini |
| 2008/0112885 A1 | 5/2008 | Okunev et al. |
| 2008/0146890 A1 | 6/2008 | LeBoeuf et al. |
| 2008/0171945 A1 | 7/2008 | Dotter |
| 2008/0198872 A1 | 8/2008 | Pierce |
| 2008/0214903 A1 | 9/2008 | Orbach |
| 2008/0293453 A1 | 11/2008 | Atlas et al. |
| 2009/0010461 A1 | 1/2009 | Klinghult et al. |
| 2009/0024045 A1 | 1/2009 | Prakash et al. |
| 2009/0037575 A1 | 2/2009 | Crystal et al. |
| 2009/0117883 A1 | 5/2009 | Coffing et al. |
| 2009/0144080 A1 | 6/2009 | Gray et al. |
| 2009/0149767 A1 | 6/2009 | Rossetti |
| 2009/0156908 A1 | 6/2009 | Belalcazar et al. |
| 2009/0171170 A1 | 7/2009 | Li et al. |
| 2009/0209873 A1 | 8/2009 | Pinter et al. |
| 2009/0279389 A1 | 11/2009 | Irie |
| 2009/0287067 A1 | 11/2009 | Dorogusker et al. |
| 2009/0312655 A1 | 12/2009 | Lo |
| 2010/0027379 A1 | 2/2010 | Saulnier et al. |
| 2010/0033303 A1 | 2/2010 | Dugan et al. |
| 2010/0042008 A1 | 2/2010 | Amitai et al. |
| 2010/0049006 A1 | 2/2010 | Magar et al. |
| 2010/0094152 A1 | 4/2010 | Semmlow |
| 2010/0113950 A1 | 5/2010 | Lin et al. |

(56) References Cited

U.S. PATENT DOCUMENTS

| | | | |
|---|---|---|---|
| 2010/0148956 A1 | 6/2010 | Song et al. |
| 2010/0184479 A1 | 7/2010 | Griffin, Jr. |
| 2010/0204758 A1 | 8/2010 | Boon et al. |
| 2010/0217099 A1 | 8/2010 | LeBoeuf et al. |
| 2010/0217100 A1 | 8/2010 | LeBoeuf et al. |
| 2010/0217345 A1 | 8/2010 | Wolfe et al. |
| 2010/0256509 A1 | 10/2010 | Kuo et al. |
| 2010/0281261 A1 | 11/2010 | Razzell |
| 2010/0298711 A1 | 11/2010 | Pedersen et al. |
| 2010/0324378 A1 | 12/2010 | Tran et al. |
| 2011/0015496 A1 | 1/2011 | Sherman et al. |
| 2011/0035927 A1 | 2/2011 | Griffin et al. |
| 2011/0134725 A1 | 6/2011 | Su et al. |
| 2011/0235466 A1 | 9/2011 | Booij et al. |
| 2011/0301439 A1 | 12/2011 | Albert et al. |
| 2012/0051187 A1 | 3/2012 | Paulson |
| 2012/0127833 A1 | 5/2012 | Ghen et al. |
| 2012/0147921 A1 | 6/2012 | Conti et al. |
| 2012/0157019 A1 | 6/2012 | Li |
| 2012/0158090 A1 | 6/2012 | Chavan et al. |
| 2012/0171963 A1 | 7/2012 | Tsfaty |
| 2013/0197320 A1 | 8/2013 | Albert et al. |

FOREIGN PATENT DOCUMENTS

| | | |
|---|---|---|
| CN | 102347804 A | 2/2012 |
| DE | 2506936 A | 9/1976 |
| DE | 4212670 A1 | 1/1994 |
| EP | 631226 A1 | 12/1994 |
| FR | 2740426 A1 | 4/1997 |
| GB | 2181554 A | 4/1987 |
| JP | 59-122032 A | 7/1984 |
| JP | 59-190742 A | 10/1984 |
| JP | 63-072231 A | 4/1988 |
| JP | 63-294044 A | 11/1988 |
| JP | 1-244328 A | 9/1989 |
| JP | 5-167540 A | 7/1993 |
| JP | 6-326669 A | 11/1994 |
| JP | 2002191562 A | 7/2002 |
| JP | 2002-261731 A | 9/2002 |
| JP | 2003-010177 A | 1/2003 |
| JP | 2005-295378 A | 10/2005 |
| JP | 2012-065073 A | 3/2012 |
| MX | 2009011781 A1 | 5/2011 |
| WO | WO 82/00910 A1 | 3/1982 |
| WO | WO 88/05282 A1 | 7/1988 |
| WO | WO 90/08361 A1 | 7/1990 |
| WO | WO 92/06551 A1 | 4/1992 |
| WO | WO 97/31437 A1 | 8/1997 |
| WO | WO98/38611 A1 | 9/1998 |
| WO | WO00/41620 A1 | 7/2000 |
| WO | WO 01/57619 A2 | 8/2001 |
| WO | WO2004/037080 A1 | 5/2004 |
| WO | WO2007/014545 A2 | 2/2007 |
| WO | WO 2008/066682 A2 | 6/2008 |
| WO | WO2010/113354 | 10/2010 |
| WO | WO 2010/144626 A1 | 12/2010 |
| WO | WO 2011/006356 A1 | 1/2011 |
| WO | WO 2011/008838 A1 | 1/2011 |
| WO | WO 2011/014292 A1 | 2/2011 |
| WO | WO 2011/022942 A1 | 3/2011 |
| WO | WO 2011/040877 A1 | 4/2011 |
| WO | WO 2011/137375 A2 | 11/2011 |

OTHER PUBLICATIONS

Australian Design Awards; Heartplus Micro; printed from website http://www.designawards.com/au on Apr. 12, 2002; 6 pgs.
Bajaj, M.D.; Event Recording in Ambulatory Patients with Syncopal Events; University of Kansas; Wichita, Kansas; (no date); pp. 15-18; printed on or before Apr. 14, 2010.
Bluetooth; Headset Profile (HSP); printed from website http://bluetooth.com/English/Technology/Works/Pates/HSP.aspx, printed May 12, 2010; 1 pg.
Bramanti et al., Multichannel telemetric system for biomedical signals via switched telephone lines; Medical and Biological Engineering and Computing, Sep. 1982, vol. 20, No. 5, pp. 653-656.
Burke, A Micropower Dry-Electrode ECG Preamplifier; IEEE Transactions on Biomedical Engineering, Feb. 2000, vol. 47, No. 2, pp. 155-162.
Card Guard; CG-6108 ACT Ambulatory Cardiac Telemetry Brochure; Card Guard, The Telemedicine Company: Switzerland; (year of publication is sufficiently earlier than the effective U.S. filing date and any foreign priority date) 2006; 2 pgs.
Cardiocomm Solutions; GEMS Air (PC based ECG management); printed from website http://www.cardiocommsolutions/com on Mar. 19, 2010; 1 pg.
Charuvastra; Transtelephonic Cardiac Event Recording for Arrhythmia Surveillance; printed from website http://tchin.org/resource_room/c_art on Mar. 26, 2010; 2 pgs.
Cheng, Allen C.; Real-Time Cardiovascular Diseases Detection on a Smartphone; printed Apr. 14, 2010.
Company-Bosch et al.; ECG Front-End Design is Simplified with MicroConverter; Analog Dialogue; Nov. 2003; vol. 37(11); pp. 1-5.
Creative; PC-80B Portable ECG Monitor w/sd card extension slot; printed from website www.amazon.com/Portable-Monitor-extension-leather-shipping/dp/B001OjWKUE on Feb. 4, 2010; 3 pgs.
Deveau, Health care eyes smart phones to heal ills (posted Sep. 15, 2009); printed from website http://www.theQiobeandmail.com on Sep. 17, 2009, 4 pages.
Dobrev, et al.; Bootstrapped two-electrode biosignal amplifier; Med Biol Eng Comput; vol. 46(6); Jun. 2008, pp. 613-619.
Elert, Glenn (Editor); Frequency Range of Human Hearing; The Physics Factbook; web version as of Mar. 29, 2010; 2 pgs.; printed Jun. 6, 2012 (http://web.archive.org/web/20100329141847/http://hypertextbook.com/facts/2003/ChrisDAmbrose.shtml).
Favorite Plus; Handheld Easy ECG Monitor; (Product ID: FP180); printed from website www.favoriteplus.com/easy-ecg-handheld-monitor-fp180 on Feb. 4, 2010; 2 pgs.
Favorite Plus; Handheld ECG Monitor—Handheld EKG Monitor at Favoriteplus.com (Products: FP180, FP-RMH and FP-ICH); printed from website www.favoriteplus.com/handheld-ecg-ekg-monitor.php on Feb. 4, 2010; 3 pgs.
Favorite Plus; Handheld EKG Monitor InstantCheck; (Product ID: FP-ICH); printed from website http://www.favoriteplus.com/instanchcheck-hand held-ecg-ekg-monitor on Feb. 4, 2010; 2 pgs.
Ferrick, M.D., Holter Monitoring and Cardiac Event Recording in Assessing Symptomatic Patients; Albert Einstein College of Medicine; Bronx, New York; (no date); pp. 11-14; printed on or before Apr. 14, 2010.
Fulford-Jones, et al., A Portable, Low-Power, Wireless Two-Lead EKG System; Proc. of the 26th Ann. Int. Conf. IEEE EMBS; San Francisco, CA, USA; Sep. 1-5, 2004, pp. 2141-2144.
Gillette, M.D.; Diagnosis of Pediatric Arrhythmias with Event Recording; Medical University of South Carolina; Charleston, South Carolina; (no date); pp. 25-32; printed on or before Apr. 14, 2010.
Grier, James W.; How to use 1-lead ECG recorders to obtain 12-lead resting ECGs and exercise ("stress") ECGs; printed from website http://www.ndsu.edu/pubweb/grier on Jun. 7, 2010; 13 pgs.
Hannaford, Kat; How to Turn Your iPhone Into a Laser, Fan or Flashlight; printed from website http://m.gizmodo.com/5534904; printed Feb. 3, 2011.
Hayes, M.D., Approaches to Diagnosing Transient Arrhythmias—An Overview; Mayo Clinic; Rochester, Minnesota; (no date); pp. 7-10; printed on or before Apr. 14, 2010.
Hearing Loss Assoc. of Kentuckiana; Decibal Ratings/Hazardous Time Exposures of Common Noise (excerpt from Survivor's Manual); web version as of Oct. 5, 2008; 2 pgs.; printed Jun. 6, 2012 (http://web.archive.org/web/20081005143856/http://www.hearinglossky.org/hlasurvival1.html).
Huang, Tina; Age-related hearing loss; Minnesota Medicine; 90(10); pp. 48-50; Oct. 2007; printed Jun. 6, 2012 from: http://www.minnesotamedicine.com/PastIssues/PastIssues2007/October2007/ClincalHuangOctober2007.aspx).
IMEC News; IMEC extends flexible ECG patch to enable arrhythmia detection; printed from website http://www2.imec.be/imec on Aug. 18, 2009; 1 pg.

(56) References Cited

OTHER PUBLICATIONS

Instromedix; Cardiac Event Recording FAQs; Instromedix: A Card Guard Company, San Diego, CA; printed from website www.instromedix.com/pdf/products/cardiac; printed on or before Apr. 14, 2010.
Instromedix; The Arrhythmia Monitoring System; King of Hearts Express AF Recorder Brochure; from Instromedix; A CardGuard Company; Rosemont IL; (year of publication is sufficiently earlier than the effective U.S. filing date and any foreign priority date) 2004; 3 pgs.
iRHYTHM; Zio(TM) Patch; printed from website http://www.irhythmtech.com/zio-solution/zio-pach/, printed Apr. 12, 2010.
Kim, et al., Detection of Atrial Fibrillation Episodes using Multiple Heart Rate Variability Features in Different Time Periods; Conf Proc IEEE Eng Med Biol Soc.; EMBS; 30th Ann. Int. Conf.; Aug. 20-25, 2008, 5482-5485.
Koerner; The Author's Metrics; Wired Magazine Article; New York, NY; Jul. 2009; pp. 93-126.
Kumparak, Greg; Visa officially announces their case that turns your iPhone into a credit card (and we've got pics!); May 17, 2010; www.mobilecrunch.com; printed Feb. 3, 2011.
Leijdekkers et al., Trial Results of a Novel Cardiac Rhythm Management System using Smart Phones and Wireless ECG Sensors; Proc. of the 7th Int. Conf. on Smart homes and health Telematics., Tours, France; Jul. 1-3, 2009; 8 pgs.
Levkov et al., Removal of power-line interference from the ECG: a review of the subtraction procedure; BioMedical Engineering Online; 4:50; Aug. 23, 2005; 18 pgs.; (printed from website http://www.biomedical-engineeringonline.com/content/4/1/50).
M Med Choice; (company information page) Beijing Choice Electronic Technology Co., Ltd.; printed from website http://www.choicemmed.com/1xwm .asp; printed Dec. 28, 2009; 1 page.
M Med Choice; Handheld ECG Monitor Brochure; MD100 Products; Beijing Choice Electronic Technology Co. Ltd.; 6 pgs; published on or before Apr. 14, 2010.
M Med Choice; Handheld ECG Monitor MD100A1; printed from website http://www.choicemmed.com/productshow.asp on Dec. 28, 2009; 2 pgs.
M Med Choice; Handheld ECG Monitor MD100B; printed from website http://www.choicemmed.com/productshow.asp on Dec. 28, 2009; 2 pgs.
Mauvila: Mauvila ECG Tutorial; Basic ECG Interpretation Tutorial; Sections 1-12; 2004; printed from website http://mauvila.com/ECG/ecg.htm on Mar. 26, 2010; 57 pgs.
Medgadget; Zio(TM) Patch Wins Medical Design Award; MedGadget internet journal of emerging medical technologies; printed from website http://medgadget.com/archives/2010/04/zio patch wins medial desian award 1.html on Apr. 12, 2010; 1 pg.
MiCardioMobile: Remote Wireless Cardiac Rehabilitation Monitoring printed from website; http://alivetec.cable.nu/cardiomobile; 1 page; printed Apr. 14, 2010.
Mobility Mind; Use your Treo 650 as a portable ECG monitoring device; Mobility Mind; Sep. 14, 2005, printed from website http://www.treotoday.net/2005/09/14/use-your-treo-650-as-a-portable-ecg-monitoring-device/ (accessed Mar. 26, 2010); 1 pg.
Muench, Frederick PhD; HRV: The Manufacturers and Vendors Speak; The portable StressEraser Heart Rate Variability Biofeedback Device: Background and Research; Biofeedback; vol. 36, Iss. 1; pp. 35-39; Spring 2008.
Murph; RedEye mini converts iPhone, iPad or iPod touch into IR-beaming universal remote; printed from website http://www.engadget.com/2010/03/02/redeye on Mar. 2, 2010; 2 pgs.
Neuroreille; Audiometry; web version as of Oct. 14, 2008; 1 pg.; printed Jun. 6, 2012 (http://www.neuroreille.com/promenade/english/audiometry/audiometry.htm).
Omron; Omron Portable ECG EKG Handheld HCG-801 Monitor; printed from website http://www.amazon.com/Omron-Portable-Handheld-HCG-801-Monitor/dp/B0019WH3EO on Feb. 24, 2010; 4 pgs.
Omron; Omron Portable ECG Monitor; printed from website http://www.target.com/gp/detail.html on Mar. 26, 2010; 1 pg.
Oresko, et al., Detecting Cardiovascular Diseases via Real-Time Electrocardiogram Processing on a Smartphone; 2009 Workshop on Biomedicine in Computing: Systems, Architectures, and Circuits (BiC); Austin, TX; Jun. 2009; pp. 13-16.
Perez, Sarah; No NFC? No Problem; New Startup Zoosh Provides Workaround Technology (Jun. 20, 2011); printed on or before Jun. 27, 2011 from website; 2 pgs.; (http://www.readwriteweb.com/archives).
Prystowsky, M.D., Chairmans Introduction; Duke University Medical Center; Indianapolis, Indiana; pp. 5-6; printed on or before Apr. 14, 2010.
Prystowsky, M.D., Chairmans Summary; Duke University Medical Center; Indianapolis Indiana; (no date); pp. 39-40; printed on or before Apr. 14, 2010.
Prystowsky, M.D., The Clinical Application, Diagnostic Yield and Cost Considerations of Cardiac Event Recorders; Duke University Medical Center; Indianapolis Indiana; (no date); pp. 19-23 printed on or before Apr. 14, 2010.
Puurtinen, et al., Best Electrode Locations for a Small Bipolar ECG Device: Signal Strength Analysis of Clinical Data, Annals of Biomedical Engineering, vol. 37, No. 2, Feb. 2009; pp. 331-336.
Raju; Heart-Rate and EKG Monitor Using the MSP430FG439 (Application Report); Texas Instruments; SLAA280-Oct. 2005-(Revised Sep. 2007); 11 pgs.
Read-My-Heart; ECG Machine Handheld Read My Heart; (Product Item No. HH-3413); printed from website http://www.helioliving.com/ECG-Machine-Handheld-ReadMyHeart on Feb. 4, 2010; 1 pg.
Read-My-Heart; ReadMyHeart Personal Handheld ECG Monitor with Free Illustrator Book & Free Electrodes V2.2; printed from website http://www .amazon.com/Readmyheart-Personai-Handheld-illustrator-Electrodes/dp/B0010AN63W on Mar. 26, 2010; 1 pg.
Ricker; Square payment dongle demoed for iPhone toting hippies and you (video); printed from website http://www.engadget.com/2010/01/18/square-payment on Jan. 18, 2010; 6 pgs.
Rockwood; Interviews: The Networked Body Magazine Article from Fast Talk Magazine; Jul. 2009; pp. 19-26.
Salahuddin, et al., Ultra Short Term Analysis of Heart Rate Variability using Normal Sinus Rhythm and Atrial Fibrillation ECG Data; e-Health Networking, App. and Services; 9th Int. Conf.; IEEE; Taipei, TW; pp. 240-243; Jun. 19-22, 2007.
Semler, M.D.; The Future of Cardiac Event Monitoring; St. Vincent Hospital and Medical Center; Portland, Oregon; (no date); pp. 33-37; printed on or before Apr. 14, 2010.
SFO Medical; Choice Portable Handheld ECG EKG Monitor; printed from website http://www.amazon.com/Choice-Portable-Handheld-ECG-Monitor/dp/B001Q74VOM on Mar. 26, 2010; 1 page.
Shenzen New Element Med. Equipment; Wireless ECG Monitoring System; printed from website http://www.alibaba.com/product-gs/248168581/Wireless ECG Monitoring system. html. On Mar. 26, 2010.
Smith; Smartphone may keep the cardiologist away; The Independent; Mar. 5, 2010; printed from website http://www.independent.co.uk/life-style/health-and-families/health-news/smartphone-may-keep-the-cardiologist-away-1916652.html on Mar. 26, 2010.
Stevens, Tim; Apple's Seamlessly Embedded Heart Rate Monitor could turn theiPhone into a new-age mood ring (posted May 6, 2010); printed from website www.engadget.com on May 6, 2010; 3 pgs.
Taleb Medical; Observer Hand-held ECG Monitor MD100B; printed on or before Apr. 14, 2010.
Texas Instruments; Information for Medical Applications, Biophysical Monitoring—Electrocardiogram (ECG) Front End; Apr. 2004, pp. 17-18.
Tschida (posted by); Power A's New Case Turns Your iPhone Into a Universal Remote; printed from website http://appadvice.com/appnn on Mar. 1, 2010; 2 pgs.
Vanhemert, Kyle; XWave Headset Lets You Control iPhone Apps With Your Brain; Sep. 8, 2010; printed from website http://gizmodo.com; printed Sep. 8, 2010.

(56) References Cited

OTHER PUBLICATIONS

FREE2MOVE; Vitaphone 2300; www.free2move.us/News/NewsVitaphone240105.htm; printed May 12, 2010; 2 pgs.

Wikimedia Laboratories; Acoustics; web archive version dated Jan. 25, 2009; 2 pgs.; printed Jun. 6, 2012 (http://liveweb.archive.org/http://en.labs.wikimedia.org/wiki/Acoustics).

Wikipedia; Aliasing; web version as of Apr. 3, 2011; 5 pgs.; printed Jun. 6, 2012 (http://liveweb.archive.org/http://en.wikipedia.org/w/index.php?title=Aliasing&oldid=422141882).

Wikipedia; Hearing Range; web version as of Feb. 6, 2010; 5 pgs.; printed Jun. 6, 2012 (http://web.archive.org/web/20100206213741/http://en.wikipedia.org/wiki/Hearing_range).

Wikipedia; Pulse oximetry; printed from website httg://en.wikipedia.org on May 10, 2010, 4 pages.

Woodward et al.; Bio-Potential-To-Frequency Converter/Modulator; Electronic Design; Aug. 9, 1999; p. 117.

Ziegler, Chris; EPI Life phone sports ECG function, can let doctors know if you're not gonna make it; printed from website http://www.engadget.com/2010/06/16/epi-life-phonesports on Jun. 17, 2010; 4 pgs.

Jenkins II, W.; Time/Frequency Relationships for an FFT-Based Acoustic Modem; Naval Postgraduate School; pp. 1-102; Sep. 2010 (http://edocs.nps.edu/npspubs/scholarly/theses/2010/Sep/10Sep_Jenkins.pdf) printed Oct. 2, 2013.

Modem Protocols Explained; ftp://kermit.columbia.edu/kermit/cu/protocol.html; 5 pgs.; printed Oct. 2, 2013.

Modem Tutorial; http://www.lsu.edu/OCS/its/unix/tutorial/ModemTutorial/ModernTutorial.html; 2 pgs.; printed Oct. 2, 2013.

Nam et al.; An Ultrasonic Sensor Based Low-Power Acoustic Modem for Underwater Communication in Underwater Wireless Sensor Networks; Computer Network Lab, Dept. of Elec. Eng., Korea Univ.; pp. 494-504; Dec. 2007 (http://nesl.ee.ucla.edu/fw/torres/home/Dropbox/good_paper_mico_controller.pdf; 11 pgs.; printed Oct. 2, 2013).

Shumaker, J.; Designing an Ultrasonic Modem for Robotic Communications; Army Research Laboratory; 26 pgs.; Mar. 2009 (http://www.dtic.mil/cgi-bin/GetTRDoc?AD=ADA499556) printed Oct. 2, 2013.

Tei, et al., New index of combined systolic and diastolic myocardial performance: a simple and reproducible measure of cardiac function—a study in normals and dilated cardiomyopathy; J Cardiol.; 26(6):357-366; Dec. 1995.

Wisneski, C.; Ultrasonic Local Area Communication; http://alumni.media.mit.edu/~wiz/ultracom.html; 2 pgs.; printed Oct. 2, 2013.

Albert et al.; U.S. Appl. No. 13/969,446 entitled "Ultrasonic Transmission of Signals," filed Aug. 16, 2013.

Albert et al.; U.S. Appl. No. 13/964,490 entitled "Heart Monitoring System Usable with a Smartphone or Computer," filed Aug. 12, 2013.

Dinh; Heart Activity Monitoring on Smartphone; IPCBEE-Int Conf Biomedical Eng and Technol; 11:45-49; Jun. 17-19, 2011.

* cited by examiner

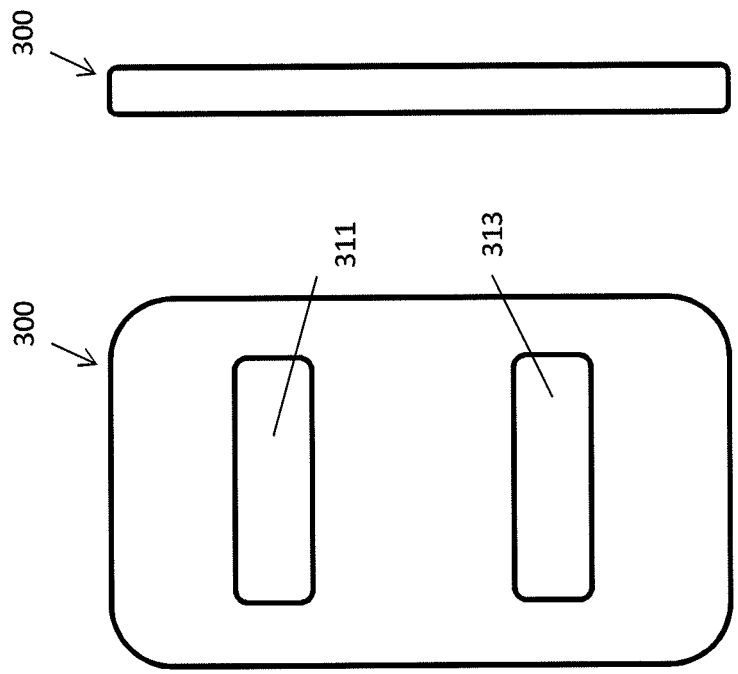
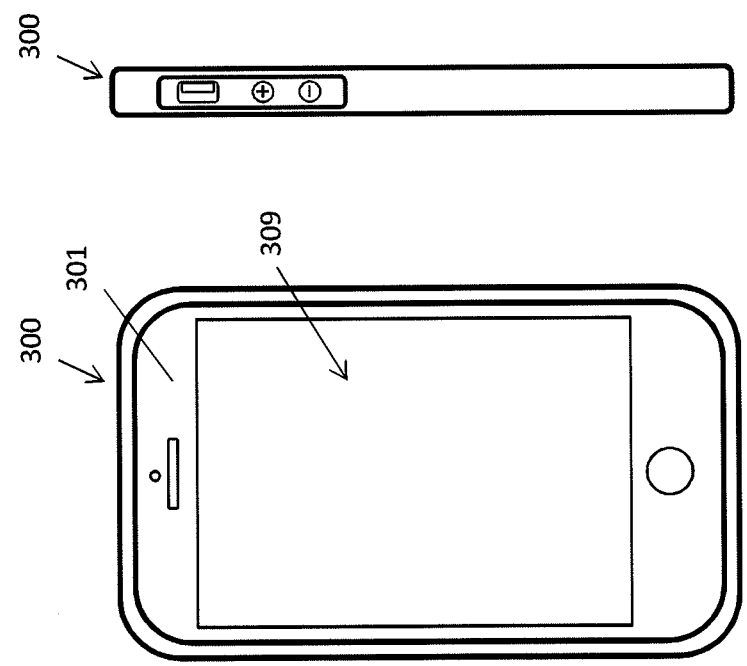
FIG. 3E
FIG. 3D
FIG. 3C
FIG. 3B

CARDIAC PERFORMANCE MONITORING SYSTEM FOR USE WITH MOBILE COMMUNICATIONS DEVICES

CROSS REFERENCE TO RELATED APPLICATIONS

This patent application claims priority to U.S. Provisional Patent Application No. 61/695,278, filed Aug. 30, 2012 and titled "CARDIAC PERFORMANCE MONITORING SYSTEM FOR USE WITH MOBILE COMMUNICATIONS DEVICES," which is herein incorporated by reference in its entirety.

This material may be related to: U.S. patent application Ser. No. 13/964,490, filed Aug. 12, 2013 and titled "HEART MONITORING SYSTEM USABLE WITH A SMARTPHONE OR COMPUTER," which is a divisional of U.S. patent application Ser. No. 12/796,188, filed Jun. 8, 2010 and titled "HEART MONITORING SYSTEM USABLE WITH A SMART PHONE OR COMPUTER," now U.S. Pat. No. 8,509,882; U.S. patent application Ser. No. 13/108,738, filed May 16, 2011 and titled "WIRELESS, ULTRASONIC PERSONAL HEALTH MONITORING SYSTEM," now Publication No. US-2011-0301439-A1; and U.S. Pat. No. 8,301,232, filed Mar. 14, 2012 and titled "WIRELESS, ULTRASONIC PERSONAL HEALTH MONITORING SYSTEM," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This patent application discloses inventive concept(s) related generally to systems, methods and devices, including hardware, firmware and software, for measuring and/or analyzing cardiac function in a user or patient with mobile communications and/or computing devices such as smartphones. In particular, described herein are methods, devices and systems for using a mobile telecommunications device to measure one or more parameters including cardiac parameters such as seismocardiograms. The system may be simple, lightweight and may adapt existing consumer mobile devices making it appropriate for home and patient-operated use.

BACKGROUND

At-home monitoring of cardiac activity and metrics of cardiac activity is an area of intense interest, because it offers the potential for vastly improving patient quality of life and life expectancy, as well as substantially reducing health care costs. For example congestive heart failure (CHF) is a common, costly, disabling, and potentially deadly condition. In developed countries, around 2% of adults suffer from heart failure, but in those over the age of 65, this increases to 6-10%. Although warning factors for CHF episodes (symptoms), including changes in cardiac rhythm, heart rate, and heart rate variability, have been identified, monitoring of patient's outside of the hospital setting has proven difficult and expensive. Thus, there is a well-established need for such (e.g., "at home") monitoring.

Congestive heart failure, myocardial infarction, and other cardiac problems are fatal to a large number of people every year. Congestive heart failure and other cardiac problems can happen suddenly and be fatal without immediate treatment. Patients with cardiac problems can feel fine after being treated by a doctor to evaluate the patient's medication intake and cardiac functions. However, cardiac problems can arise between appointments and possibly lead to fatal cardiac events.

Changes in federal regulations of Medicare can penalize hospitals for emergency room admission of patients recently treated for cardiac problems. The new penalties provide additional incentives for the hospitals and doctors to monitor the cardiac health of the patient to ensure good cardiac health between appointments or to catch possible problems before a cardiac event requiring a visit to the emergency room occurs. Therefore, improved monitoring of the cardiac health of the patient is desired. Early diagnosis of a potential symptom or problem can result in treatment that prevents a fatal cardiac event.

Described herein are methods, devices, and systems for monitoring cardiac performance that may address this need. In particular, described herein are methods and systems (including software/firmware) for using or adapting for use one or more widely available communications or telecommunications devices, such as smart phones, tablet computers, or portable computers, to monitor one or more cardiac performance indicators, including a seismocardiogram (SCG). These methods and system may record, analyze, receive, and/or send cardiac performance information (including but not limited to digital health information) and/or indicators of cardiac performance (e.g., "indexes") that may be understood by medical professionals. The devices, systems and methods may also provide direct patient feedback, both in assisting the patient to take (by themselves) a correct and/or accurate reading, and for providing an indicator of general health, including triggering an alarm. For example, a patient may record and provide access to detected health information (e.g., blood pressure, ECG, SCG, blood sugar, temperature, telemetry, etc.) to medical professionals using the methods and devices described herein. Access may be provided by uploading the medical information to a server and/or website; the website may be used to store, provide remote access to the user and/or qualified medical professionals, or analyze the health information.

Although this application focuses primarily on the use of seismocardiography using a personal communications device (e.g., smart phone), many of the principles described herein may be applied to other cardiac metrics and indices. Further, some of the principles described herein may be applied to methods and systems that may be used without a personal communications device.

Although the prior art has acknowledged the need for personal (e.g., at-home) monitoring devices, including those capable of performing and/or analyzing seismocardiography, no effective, lightweight, portable and patient-ready monitoring device has yet been developed or made available. For example, "Mechanisms Underlying Isovolumic Contraction and Ejection Peaks in Seismocardiogram Morphology" by Gurev et al. (Journal of Medical and Biological Engineering, 32(2): 103-110 (2012)) disclose a prior art setup for simultaneously taking a SCG and ECG. The equipment used in Gurev (see FIG. 1) is large, expensive, and impractical for home use. In contrast, the devices and methods disclosed herein enable the user to take an ECG and SCG at home using a hand held device, such as a mobile telecommunications device, as shown in FIG. 2.

"Seismocardiography—a non-invasive method of assessing systolic and diastolic left ventricular function in ischaemic heart disease" by Korzeniowska-Kubacka et al. (Folia Cardiol. 2006, Vol. 13, No. 4, pages 319-325) discloses using a seismocardiograph to measure cardiac function during exercise. The methods and apparatuses are administered by a medical professional in a medical office and require larger equipment that is not practical for home use or for a patient to self administer.

"A continuous, wearable, and wireless heart monitor using head ballistocardiogram (BCG) and head electrocardiogram (ECG)." By He et al. (Conf. Proc. IEEE Eng. Med. Biol. Soc. 2011, pages 4729-32) discloses a wearable heart monitoring sensor that has the form factor of a hearing aid that can communicate wirelessly with a computer device. However, the system requires the use of a separate piece, such as the in ear sensor, along with a computing device. The use of multiple pieces makes it more difficult for elderly patients to use the setup and decreases the likelihood that the patient will use the device.

U.S. Patent Application Publication No. 2009/0024045 discloses using an implanted medical device to directly measure various cardiac functions. The measurements require that the medical device is implanted within the patient's body. The methods, systems, and devices disclosed herein offer significant advantages because they do not require an invasive implanted medical device and can be used to quickly and conveniently measure a number of cardiac parameters with the patient in the comfort of their home.

U.S. Pat. No. 6,024,705 discloses using a seismic sensor to take an SCG along with a computer to analyze the waveform and output a numerical value representing cardiac performance. These devices are also impractical for home use or self-testing. The methods and devices are not used (or compatible with use) with a mobile telecommunications device.

U.S. patent application Ser. No. 12/796,188, filed Jun. 8, 2010 and titled "HEART MONITORING SYSTEM USABLE WITH A SMART PHONE OR COMPUTER," now U.S. Pat. No. 8,509,882 and U.S. patent application Ser. No. 13/108,738, filed May 16, 2011 and titled "WIRELESS, ULTRASONIC PERSONAL HEALTH MONITORING SYSTEM," now Publication No. US-2011-0301439-A1, describe ECG monitors that convert ECG data into ultrasound signals that can be received by a telecommunications device such as a smartphone and then stored, analyzed, and/or displayed. The instant application extends and adapts this teaching and may be used with any of the systems, methods, and devices described herein.

SUMMARY OF THE DISCLOSURE

In general, the devices, systems, software, and methods described herein allow an operator, including the patient, to measure a metric of cardiac performance in a simple and inexpensive fashion. The invention may operate with a pre-existing mobile telecommunication device having an accelerometer (or adapted for use with an accelerometer) without requiring additional instrumentation.

In general, the systems described herein may be referred to as cardiac performance monitoring systems. In some variations these systems may be referred to as SCG (or seismocardiogram) monitoring systems. Any of these systems may include control logic for controlling a mobile telecommunications device, and in particular, for controlling the accelerometer of a mobile telecommunications device so that it detects and in some variations records an SCG signal. A cardiac performance monitoring system may be configured to include software (an "app" or applications) for a mobile telecommunications device (e.g., mobile telecommunications devices, smart phones, etc.) that includes the control logic to control the mobile telecommunications device to use its existing components to examine, record, transmit and/or analyze a seismocardiogram. Thus, the cardiac performance monitoring system may include executable logic that controls the mobile telecommunications device to detect vibration and/or position, and to guide the user in taking readings of cardiac performance.

In some variations, the cardiac performance monitoring system may include an ECG monitoring component (e.g., electrodes, including electrodes on a case configured to hold the mobile telecommunications device as described in U.S. application Ser. No. 13/420,520). Thus the cardiac performance monitoring system may comprise a housing or case for a mobile telecommunications device having one or more electrodes. The cardiac performance monitoring system may also be used without the additional ECG monitoring electrodes.

For example, when placed on the chest of a user, the cardiac performance monitoring systems disclosed herein can cause the mobile telecommunications device to measure vibrations caused by the heartbeat to get a seismocardiogram (SCG) of the user. The user can conveniently and easily use the mobile telecommunications device to take their own SCG at their convenience, including in a home setting. This data may be stored and/or analyzed by the mobile telecommunications device, and/or transmitted to a remote location (e.g., website) for analysis, storage, or further processing, including being added to the patient's medical records, or being analyzed by a physician.

The methods and systems (cardiac performance monitoring system) described herein may also provide one or more indices of cardiac health based on the patient's SCG. In particular, the SCG detected by the mobile telecommunications device may be analyzed to determine an index of left ventricular performance. In some variations the methods and systems record both an SCG and an ECG over the same time period.

The cardiac performance monitoring system can control the telecommunications device to communicate with an ECG component to take an ECG of the patient. The SCG and ECG can be analyzed to determine the left ventricular performance of the user. The cardiac performance monitoring system can analyze the cardiac performance data to establish a baseline for the cardiac performance of the patient and to alert the patient of any statistically significant changes in the cardiac performance.

In some variations the cardiac performance monitoring system guides the patient through the procedure for measuring an indicator of cardiac performance. The cardiac performance monitoring system may also confirm the steps, including that the patient (or user) has properly positioned the device to measure cardiac performance. For example, the executable control logic may detect that the mobile telecommunications device has been placed properly on the patient's chest by confirming that the mobile telecommunications device is flat (e.g., horizontal) by controlling the accelerometer and/or gyroscope that may be built into the mobile telecommunications device (e.g., iPhone, android, etc.). Instructions and/or patient feedback may be visual, audible, tactile, or some combination of these.

Cardiac performance data can be monitored remotely by a physician or other medical professional. The physician can receive an automatic notification for any changes in the cardiac performance of the patient to evaluate changes in the mediation or treatment of the patient or the need for immediate medical treatment.

For example, described herein are apparatuses comprising non-transitory computer-readable storage medium storing a set of instructions capable of being executed by a smartphone having an accelerometer. The set of instructions, when executed by the smartphone, causes the smartphone to record a seismocardiogram (SCG) from the smartphone's accelerometer by detecting vibrations on a patient's chest corresponding to heart motion for a first time period. Further, the set of instructions, when executed by the smartphone, cause the smartphone to do at least one of: analyze the SCG to determine an index of cardiac function, display the SCG, transmit the SCG, or store the SCG.

In general, a set of instructions on a non-transitory computer-readable storage medium may comprise a program (e.g., software, firmware, or the like) that can be executed by a processor. In most of the examples described herein the processor is part of a mobile telecommunications device such as a smartphone, however, any appropriate processor may be used.

The set of instructions on the non-transitory computer-readable storage medium of may also, when executed by the smartphone, cause the smartphone to receive an electrocardiogram (ECG) from the patient, wherein the ECG is taken over the first time period. In some variations the set of instructions is configured so that it controls acquisition of the ECG as well as acquisition of the SCG. In general, the ECG and SCG may be collected/recorded over the same time period (e.g., having the same start time and/or stop time), so that the two can be time-locked or correlated. The SCG and ECG may be collected at the same time intervals when discrete sampling is performed, or at different time intervals. In some variations the ECG is collected using a device that is coupled to the smart phone. For example, an ECG electrode module may be used in conjunction with the smartphone. The ECG module may include two or more electrodes for collecting an ECG. The module may communicate with the phone either directly via a connection (e.g., into an input port such as an audio jack) or indirectly via a wireless connection (e.g., radio, ultrasound, audible, optical, induction, etc.). In some variations the set of instructions (which may be referred to herein as logic or control logic) on the non-transitory computer-readable storage medium may be configured to synchronize with the ECG module, so that collection of the ECG and SCG can also be synchronized as discussed above.

In some variations the set of instructions is configured to analyze the SCG data on the smart phone. The set of instructions, when executed by the smartphone, may be configured to cause the smartphone to analyze the SCG to determine the index of cardiac function in any appropriate manner. For example, the set of instructions may be configured to have the smart phone (e.g., a processor of the smart phone) take a ratio of the sum of isovolumetric contraction time (ICT) and isovolumetric relaxation time (IRT) divided by the left ventricle ejection time (ET). A set of instructions on a non-transitory computer-readable storage medium may, when executed by the smartphone, cause the smartphone to identify two or more characteristic regions of the SCG. As described in more detail below, the regions that the set of instructions may configure the device (e.g., smartphone) to recognize may include a time point or region corresponding to: mitral valve closure, isovolumetric contraction, aortic valve opening, rapid ejection, aortic valve closure, mitral valve opening, and rapid filling. These time points may be used to measure or otherwise derive additional information about the SCG and thus cardiac health of the subject from whom the reading was taken. Characteristic regions may generally be recognized based on the overall shape of the SCG curve(s) or average SCG cycle(s). In some variations, additional information may be used to help identify characteristic regions. For example, a synchronized ECG (or average ECG(s)) may be used to help identify one or more characteristic regions of an SCG. For example, a set of instructions, when executed by a smartphone, may cause the smartphone to identify two or more characteristic regions of the SCG using an electrocardiogram (ECG) that is taken over the first time period. When the ECG and SCG are synchronized, the R-wave peak, which is often readily recognized from an ECG signal, (including an ECG taken from a pair of electrodes on a patient's chest, as shown below) may indicate the location of the characteristic mitral closure (MC) peak, as shown in FIG. 6. Thus, the R-wave may be used as a fiduciary marker for the characteristic MC in an SCG. In general, multiple SCG cycles may be taken during the first time period of recording an SCG. Each "cycle" of an SCG cycle corresponds to a single, and complete, cardiac cycle for that patient. When the time period during which the SCG is acquired by the device is sufficiently long (e.g., extending over more than one cardiac cycle), multiple cycles may be analyzed. As mentioned above, multiple cycles may be averaged to remove spurious noise or irregularities. For example, the apparatus including the set of instructions on the non-transitory computer-readable storage medium may be configured by the set of instructions to identify multiple SCG cycles taken during first time period and to average the multiple SCG cycles. In some variations the SCG signal may be filtered, smoothed, and/or otherwise processed to enhance the signal received. High frequency filtering may be applied to remove noise. Similarly, smoothing may be performed to better identify characteristic regions of the SCG, which may be determined based on peaks in the SCG. In some variations, rather than averaging the waveforms of each (or a subset) of the SCG cycles recorded, the apparatus may be configured to average measurements taken from each (or a subset) of the SCGs. "Bad" or outlining SCG cycles may be rejected or not included in the analysis. A rolling average (or updating average) may be performed as new SCG cycles are measured. For example, the apparatus may determine for each SCG cycle the time of mitral valve closure (MC), aortic valve opening (AO), Aoritc valve closure (AC) and mitral valve opening (MO), and use these estimated times to derive values such as isolvolumetric contraction time (ICT or IVCT, equal to the time from MC to AO), ejection time (ET, equal to the time from AO to AC)), and isovolumetric relaxation time (IRT or IVRT, equal to the time from AC to MO). The derived values (ICT, ET, IRT, etc.) may be averaged by SCG cycles. These values may also be used to derive one or more indexes, and the index value may be based on the average values, or a raw index value for each SCG cycle may be averaged (or both).

In general, the non-transitory computer-readable storage medium having a set of instructions may be configured so that the set of instructions, when executed by the smartphone, causes the smartphone to instruct the patient how to record the SCG for determining an indicator of cardiac fitness/health. For example the set of instructions may instruct the subject to position the smartphone against the patient's chest prior to recording the SCG. Instructing the subject may be done by presenting visual (e.g., images, text, or both on the smartphone screen) and/or audible (using the speaker of the smartphone) instructions to the subject. The apparatus may instruct the subject/patient to place the smartphone against the chest while lying down so that the smartphone rests against the chest, substantially flat. The smartphone may also be configured by the set of instructions to monitor the position of the apparatus while recording the SCG and/or ECG and stop the recording if the patient moves too much (which may lead to erroneous readings). Thus, for example, the non-transitory computer-readable storage medium configured by the set of instructions, when executed by the smartphone, may cause the smartphone to verify the orientation of the smartphone and notify the user if the orientation of the smartphone during the first time period was incorrect.

The smartphone may also be configured to indicate when the recording is ongoing and/or when it has completed. The smartphone may also be generally configured by the instructions to indicate the outcome of the SCG (e.g., good reading, bad reading, repeat reading, etc.) including providing an output of the SCG on the smartphone.

Another example, of an apparatus is a non-transitory computer-readable storage medium in a smartphone having an accelerometer storing a set of instructions capable of being executed by the smartphone, that, when executed by the smartphone, causes the smartphone to: record a seismocardiogram (SCG) from the smartphone's accelerometer by detecting vibrations on a patient's chest corresponding to heart motion for a first time period; and receive an electrocardiogram (ECG) from the patient over the first time period; analyze the SCG to determine an index of cardiac function for the patient; and do at least one of: display, transmit and store the index of cardiac function. Any of the features discussed above may also be included in this variation. For example, the set of instructions, when executed by the smartphone, may cause the smartphone to analyze the SCG to determine an index of cardiac function for the patient by identifying characteristic regions of the SCG using the ECG, such as by identifying two or more of: mitral valve closure, isovolumetric contraction, aortic valve opening, rapid ejection, aortic valve closure, mitral valve opening, and rapid filling. The set of instructions, when executed by the smartphone, may cause the smartphone to analyze the SCG to determine an index of cardiac function for the patient by taking a ratio of the sum of isovolumetric contraction time (ICT) and isovolumetric relaxation time (IRT) divided by the left ventricle ejection time (ET).

Methods of estimating cardiac fitness/health are also described, including methods of using the apparatuses described above. For example, a method of determining an index of cardiac function for a patient using a smartphone having an accelerometer may include: placing the smartphone on the patient's chest; recording a seismocardiogram (SCG) for a first time period using the smartphone's accelerometer; and analyzing the SCG to determine an index of cardiac function.

In any of these variations, the method may also include the step of receiving an electrocardiogram (ECG) in the smartphone, wherein the ECG is recorded from the patient over the first time period. The received ECG may be synchronized with the SCG. The synchronization may be controlled by the logic running on the smartphone, which may trigger both the recordings of the ECG and SCG, or the logic may be configured to passively wait for the ECG recording to begin and thereafter trigger reading of SCG, although the time basis may be the same (e.g., the SCG and ECG may be time locked, sharing the same time axis).

In general, the apparatuses described herein may be used by a patient to help determine his or her own cardiac health. Thus, these devices may be used in a home or other non-clinical setting. The results may be transmitted to a clinician (physician, nurse, technician, etc.) immediately or after a delay, and/or placed in the patients file (e.g., electrical medical record). Thus, any of these methods and devices may be used by the patient/subject himself or herself, and may include instructions guiding the user (the patient/subject or a family member) in how to use the apparatus. For example, the step of placing the smartphone on the patient's chest may comprise the patient placing the smartphone on the patient's own chest; the apparatus may tell and/or show the patient how to correctly place the apparatus.

In any of these variations the method may also include using the smartphone to verify the orientation of the smartphone on the patient's chest before or during the first time period. For example, an internal gyroscope, level, or the like, may be used to determine and/or verify the orientation of the smartphone before and/or during recording of the SCG.

Analyzing the SCG to determine an index of cardiac function may include analyzing the SCG using the smartphone to determine the index of cardiac function, for example, by taking a ratio of the sum of isovolumetric contraction time (ICT) and isovolumetric relaxation time (IRT) divided by the left ventricle ejection time (ET). The method may be used to determine any index of cardiac function, including (but not limited to) the modified Tei index. In some variations, analyzing the SCG to determine an index of cardiac function comprises identifying multiple SCG cycles taken during first time period and averaging the multiple SCG cycles. Averaging may be performed at the level of the waveform (e.g., averaging each SCG cycle waveform after aligning them, e.g., by MC), or at the level of the characteristics extracted from each SCG cycle (such as the ICT, ET, IRT, etc.). In some variations, analyzing the SCG to determine an index of cardiac function comprises identifying multiple SCG cycles taken during the first time period using an electrocardiogram (ECG) that was recorded from the patient over the first time period Analyzing the SCG to determine an index of cardiac function may comprise identifying two or more characteristic regions of the SCG from the regions consisting of: mitral valve closure, isovolumetric contraction, aortic valve opening, rapid ejection, aortic valve closure, mitral valve opening, and rapid filling.

In any of the methods described herein, the SCG, including the SCG waveform and/or an indicator of the quality of the SCG waveform, or a proxy for an SCG waveform (indicating that an SCG waveform was taken) may be displayed by the smartphone. The smartphone may also or alternatively display an ECG and/or the index for cardiac health, or a simplified indicator of the index (red light/danger, green light/good, yellow light/caution, etc.).

In any of these variations the method may also include transmitting the SCG and/or extracted information from the SCG and/or ECG. For example the SCG waveform(s) and/or the ECG waveforms may be transmitted to another processor for analysis, rather than performing the analysis on the smartphone, or in addition to performing the analysis on the smartphone. For example, the method may include the step of transferring the SCG and ECG data (and/or waveforms) to a remote server over the internet for storage and/or analysis.

Another example of a method of determining an index of cardiac function for a patient using a smartphone having an accelerometer includes the steps of: placing the smartphone on the patient's chest; recording a seismocardiogram (SCG) for a first time period using the smartphone's accelerometer; receiving an electrocardiogram (ECG) in the smartphone, wherein the ECG is recorded from the patient over the first time period; and analyzing the SCG to determine an index of cardiac function. Any of the steps described above may be applied in this exemplary method as well. For example, the method may include using the smartphone to verify the orientation of the smartphone on the patient's chest before or during the first time period. As mentioned, analyzing the SCG to determine an index of cardiac function may comprise analyzing the SCG using the smartphone to determine the index of cardiac function by taking a ratio of the sum of isovolumetric contraction time (ICT) and isovolumetric relaxation time (IRT) divided by the left ventricle ejection time (ET).

BRIEF DESCRIPTION OF THE DRAWINGS

FIGS. 3B, 3C, 3D, and 3E show front, right side, back and left side, views respectively, of another variation of an apparatus including a mobile telecommunications device configured for detecting SCG and/or ECG.

DETAILED DESCRIPTION

Figure 1:
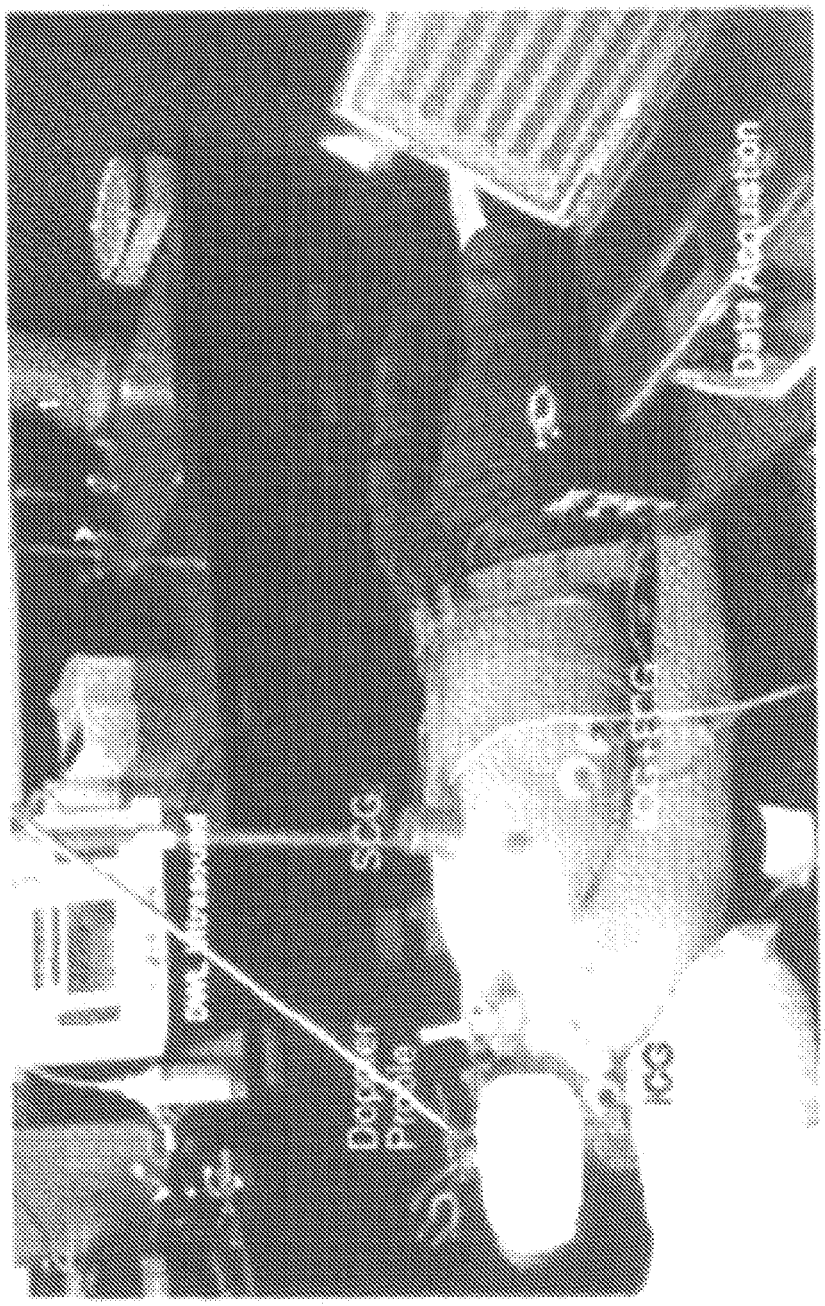
FIG. 1 is a picture of a prior art method for measuring a seismocardiogram (SCG) and electrocardiogram (ECG) for a patient. The image is adapted from FIG. 3 of "Mechanisms Underlying Isovolumic Contraction and Ejection Peaks in Seismocardiogram Morphology" by Gurev et al. (Journal of Medical and Biological Engineering, 32(2): 103-110 (2012)).

In general, described herein are apparatuses (e.g., systems and devices, including software) and methods for determining one or more indicators of a subject's cardiac health using a mobile telecommunications device (e.g., smartphone). In particular, described herein are cardiac performance monitoring apparatuses controlling a mobile telecommunications device (e.g., smartphone) to detect and/or analyze a patient's seismocardiogram (SCG). The mobile telecommunications device typically includes an integrated accelerometer and optionally a gyroscope. The methods and apparatuses described herein control operation of the mobile telecommunications device to use the accelerometer to detect a seismocardiogram and/or ballistocardiogram. For example, the accelerometer can be used to detect heart vibrations of the subject. As used herein a "subject" may be referred to as a patient or user. Heart vibrations may be used to get a seismocardiogram (SCG). In some variations the apparatus may control operation of the mobile telecommunications device to analyze the SCG on the mobile telecommunications device and/or upload the SCG to a remote site where it can be analyzed or further analyzed.

In some variations, the apparatus may be used with or may include a systems (e.g., subsystem) having one or more sensors (and particularly integral sensors) for measuring electrocardiograms with the mobile telecommunications device. For example, the methods or systems may include a case connectable to the mobile telecommunications device so that it forms an integral device not much larger than the mobile telecommunications device that can detect both SCG and ECG. The ECG sensor (electrodes) can be integral to the mobile telecommunications device or attached to a case for the mobile telecommunications device. Two or more electrodes may be used to measure the electrical characteristics of the user or patient to take an ECG. In some variations the electrodes (e.g., on a case for the mobile telecommunications device) communicate wirelessly with the telecommunications device, including transmitting coded data using an ultrasonic transmission. The SCG and ECG can be analyzed to determine the left ventricular performance of the patient or user. The methods or systems may simultaneously detect SCG and ECG data.

The apparatuses and methods disclosed herein are generally adapted for use with mobile telecommunications devices. This mobile telecommunications device may be placed on the patient's chest so that the accelerometer of the mobile telecommunications device can measure vibrations in the chest to take an SCG. In variations including ECG electrodes (e.g., when the mobile telecommunications device is housed in a case having electrodes for measuring an ECG), the electrodes can be used to measure electrical impulses on the chest to take an ECG. The mobile telecommunications device and electrodes can be used to measure cardiac parameters previously measured using larger equipment, requiring a technician, and/or multiple accessories or attachments.

The apparatuses and methods disclosed herein can be used by the patient to monitor a number of physical parameters using a handheld device, such as a mobile telecommunications device (e.g., smartphone). The patient can use the device to measure the cardiac parameters in the comfort of their home. The parameters or trend in the measured parameters can be analyzed to look for any possible indications of a problem with the patient's cardiac health.

In some variations, described herein are systems including a case device that may be used with a mobile telecommunications device. The case device may hold the mobile telecommunications device so that it forms an integrated (single piece) unit than can be placed on the patient's chest to measure SCG and/or ECG as well as other cardiac parameters. Many of the patients with decreased cardiac health are older in age, therefore it is important for the device to be convenient and easy to use at home. Separate pieces and complicated designs can be overwhelming for some users thereby discouraging the patients from using the device. Separate pieces can also be easy to lose and more difficult to use for older patients.

The convenience for the patient to quickly and easily measure the biological parameters is important because it can increase patient use. The more often the patient can measure their biological parameters the greater the benefits for the patient. Tracking the patient's cardiac function can provide more data on the cardiac health of the patient and improve the overall medical treatment. Additional data on the cardiac health trends of the patient can increase the likelihood of early diagnosis of potential cardiac problems allowing for earlier treatment and increased chances for resolving the problems prior to a catastrophic cardiac event requiring hospitalization.

Prior art methods have been used to generate an ECG and SCG for the patient at the hospital or in a doctor's office. For example, prior art methods include using a 12 lead system for generating an ECG for the patient. FIG. 1 shows a setup for using a 12 lead system for generating an ECG and a large accelerometer system for generating a SCG (See "Mechanisms Underlying Isovolumic Contraction and Ejection Peaks in Seismocardiogram Morphology" by Gurev et al.

(2011)). As can be seen, this equipment requires use of a medical facility and a skilled person to setup and operate.

The methods and systems described herein can utilize a mobile telecommunications device to measure the SCG using an accelerometer that is already part of the mobile telecommunications device. The mobile telecommunications device or a remote server can be used to analyze the SCG curve to determine additional cardiac data as well as acquire and process simultaneous ECG data. The ability for the patient to use a smartphone to take an SCG is an advantage over the prior art methods because it doesn't require a trip to the doctor's office, the use of larger equipment, or a skilled person to setup and operate.

The mobile telecommunications device can have a plurality of electrodes formed integrally to the exterior of the device, or on a case or attachment to the mobile telecommunications device, as illustrated in FIGS. 3A and 3B-3E. A case for a mobile telecommunications device can also include a plurality of electrodes. For example, U.S. patent application Ser. No. 12/796,188, filed Jun. 8, 2010 and titled "HEART MONITORING SYSTEM USABLE WITH A SMART PHONE OR COMPUTER," now U.S. Pat. No. 8,509,882 discloses a device that includes electrodes for generating an ECG. The device attaches to a smartphone or smartphone case. The electrodes can measure the electrical impulses on the patient's chest and take an ECG.

The systems and methods disclosed herein allow for a smartphone or handheld computing device with a small electrode attachment integral to the phone or phone case to simultaneously measure both the ECG and SCG for the patient. The simultaneously acquired and synchronized ECG and SCG data can be used to calculate and derive a number of cardiac parameters for the patient. For example, the methods and devices can control the mobile telecommunications device to determine patient heart rate, average heart rate, heart rhythm, and cardiac event timing via the ECG and SCG. In some variations one or more of these indicators of cardiac function are determined.

Index values can also be useful in determining the overall cardiac health of the patient. One known index for measuring the cardiac health of a patient is known as the Myocardial Performance Index (MPI) or the Tei index. The Tei index was disclosed in "New index of combined systolic and diastolic myocardial performance: as simple and reproducible measure of cardiac function—a study in normals and dilated cardiomyopathy" by Tei et al. (Journal of Cardiology 1995 26(6): 357-66). The systems and methods disclosed herein can be used to determine a modified Tei index for the patient, using the SCG data received by the mobile telecommunications device using the apparatuses and methods described.

Typically, the Tei index is lower in healthy patients and higher in patients with cardiac problems. An increase in the Tei index can be indicative of potential problems with cardiac functions. The methods, systems, software, and devices disclosed herein can provide an early warning for possible heart failure by tracking the modified Tei index for the patient. If the Tei index increases then it signals for the need for medical treatment or a modification in the medication that the patient takes to treat cardiac problems. The advanced notice for problems can possibly prevent catastrophic complications of cardiac failure. The Tei (or modified Tei) index is just one example of an index of cardiac function (or index of cardiac fitness) that may be determined from the SCG and/or ECG. The methods and apparatuses described herein may be used to determine other indices of cardiac health, including flow velocities (e.g., pulmonary venus flow velocity), cardiac loading (ventricular loading), and the like.

The apparatuses (e.g., devices and systems), and methods disclosed herein are advantageous over prior art apparatuses and methods because the patient can easily measure the cardiac parameters at their convenience at home using a hand held telecommunication device that does not require the use of additional accessories that can be easily lost or require complicated assembly. Additionally, the patient can make sophisticated measurements of their cardiac health without a trip to the doctor or using commercial equipment that costs many thousands of dollars and is only practical at hospitals and doctor's offices. The additional convenience allows for the patient to take their own measurements at home, instead of at the doctor's office. The additional measurements can be used to track the cardiac health of the patient over time. The systems and methods described herein allow the patient to act as their own control. The cardiac health can then be tracked over time and changes in the cardiac health relative the patient's own baseline can be determined and can identify problems at an early stage to allow for earlier treatment, such as modification of the medication or a visit to the doctor's office for evaluation.

Further, the apparatus (e.g., systems and devices) described herein may communicate with the smartphone and allow measurements and trends to be securely and/or automatically and/or wirelessly transmitted to caregivers. As used herein, the apparatus may be configured to wirelessly communicate with a mobile telecommunications device (e.g., smart phone). Although ultrasonic transmission is of particular interest, it should be understood that, as used herein, wireless communication (e.g., transmission of a signal) includes any appropriate wireless modality, including, but not limited to transmission of radio signals, microwave signals, visible light signals, infrared signals, sonic signals, ultrasonic signals, and electromagnetic induction signals. Thus, the apparatus may be configured to broadcast and/or receive via or more of: radio signals, microwave signals, visible light signals, infrared signals, sonic signals, including but not limited to ultrasonic signals, and electromagnetic induction signals.

It is to be understood that the invention is not limited in its application to the details of construction, experiments, exemplary data, and/or the arrangement of the components set forth in the following description. The invention is capable of other embodiments or of being practiced or carried out in various ways. Also, it is to be understood that the terminology employed herein is for purpose of description and should not be regarded as limiting.

In the following detailed description of embodiments of the disclosure, numerous specific details are set forth in order to provide a more thorough understanding of the disclosure. However, it will be apparent to one of ordinary skill in the art that the concepts within the disclosure can be practiced without these specific details. In other instances, well-known features have not been described in detail to avoid unnecessarily complicating the description.

Telecommunications Device

As used herein mobile telecommunications device (telecommunications devices) includes smartphones (e.g., iPhone™, Droid™ or other personal communications devices). In some variations mobile telecommunications device may also include some tablet computers (e.g., iPad™, tablet PCs, or the like), and other handheld computing devices.

The mobile telecommunications devices typically include an integral accelerometer or may be adapted to include an accelerometer. The systems described herein include executable control logic to control the accelerometer to measure vibrations on the patient's chest, such as vibrations caused by the patient's heartbeat (e.g., as, for example, x,y,z axis motion). The sampling rate for the accelerometer readings can be tied to the processor speed of the mobile telecommunications device. In some cases the accelerometer sampling rate may be on the order of 100 measurements per second. In some variations the telecommunications device may be controlled to adjust the sampling rate for the accelerometer.

The mobile telecommunications device can include a gyroscope or may be adapted to include a gyroscope. The gyroscope can be used to verify the positioning of the telecommunications device when in use by the patient, for example to verify the positioning of the telecommunications device when the device is taking the SCG.

The telecommunications devices can include a GPS sensor or may be adapted to include a GPS sensor. The GPS sensor can be used to verify the location of the telecommunications device when in use by the patient, for example to verify the location of the telecommunications device when the device is taking the SCG.

The telecommunications device can be adapted to communicate with an ECG component. The telecommunications device can communicate wirelessly with the ECG component. In some embodiments the telecommunications device can be configured to receive ultrasonic signals from the ECG component with encoded data corresponding to the ECG. Examples of ECG components and wireless (via ultrasonic transmission) data transfer of coded information that are usable with telecommunications devices are disclosed in U.S. patent application Ser. No. 12/796,188, filed Jun. 8, 2010 and titled "HEART MONITORING SYSTEM USABLE WITH A SMART PHONE OR COMPUTER," now U.S. Pat. No. 8,509,882, and U.S. patent application Ser. No. 13/108,738, filed May 16, 2011 and titled "WIRELESS, ULTRASONIC PERSONAL HEALTH MONITORING SYSTEM," now Publication No. US-2011-0301439-A1. The telecommunications devices can include (or may be adapted to include) a microphone capable of receiving ultrasonic sound. A telecommunications device may include logic for translating the digital signal encoded by the ultrasonic sound into a digital signal that can be displayed, uploaded/transmitted, stored, and/or analyzed.

In general, a mobile telecommunications device can include a microprocessor and logic for running software programs, such as smartphone applications. The telecommunications device can analyze and process the ECG and SCG data using a microprocessor and logic configured to control the microprocessor. The ECG and SCG data can also be uploaded to a remote server to perform the data analysis.

The cardiac performance monitoring system may control the smartphone so that it combines data and signals from other sensors built into the smartphone such as a GPS, gyroscope, and accelerometer. Further processing of this data provides additional information related to the user, such as speed, location, distance, steps, ECG, SCG, cadence, body position, fall detection and energy expenditure. The cardiac performance monitoring system may control the smartphone to take the raw signals from the sensors and so that derived information can be displayed and stored locally on the smartphone, as well as being transmitted to the web server over an internet connection. The web server may provide a web browser interface for real-time or retrospective display of the signals and information received from the smartphone, and also includes further analysis and reporting.

ECG Component

An ECG component can be included as part of a cardiac performance monitoring system, and may include an electrode assembly configured to sense heart-related signals upon contact with a user's skin, and to convert the sensed heart-related signals to ECG electrical signals. A converter assembly, integrated with, and electrically connected to the electrode assembly, may be configured to receive the ECG electrical signals generated by the sensor and output ECG sound signals through an audio transmitter to a microphone in a computing device within range of the audio transmitter. The converter assembly is further configured to output the ECG signals as an ultrasonic FM sound signal.

In one embodiment, a smartphone protective case, usable as an ECG electrode module or component, is provided as part of the cardiac performance monitoring system. An electrode assembly, configured to sense heart-related voltage signals upon contact with a user's skin, and to convert the sensed heart-related signals to an ECG differential electric signal, is provided. A converter assembly, integrated with, and electrically connected to the electrode assembly, is configured to convert the electric ECG signal generated by the electrode assembly to an ultrasonic frequency modulated ECG sound signal having a carrier frequency in the range of from about 17 kHz to about 40 kHz (e.g., about 17 kHz to about 24 kHz), and further configured to output the ultrasonic frequency modulated sound signal through an audio transmitter at a signal strength capable of being received by a smartphone positioned within the smartphone protective case.

The sensor assembly can include any suitable sensor operative to detect a physiological signal that a user desires to monitor. Nonlimiting examples of such physiological signals include, but are not limited to, respiration, heartbeat, heart rate, electrocardiogram, electromyogram (EMG), electrooculogram (EOG), pulse oximetry, photoplethysmogram (PPG) and electroencephalogram (EEG).

Figure 4:
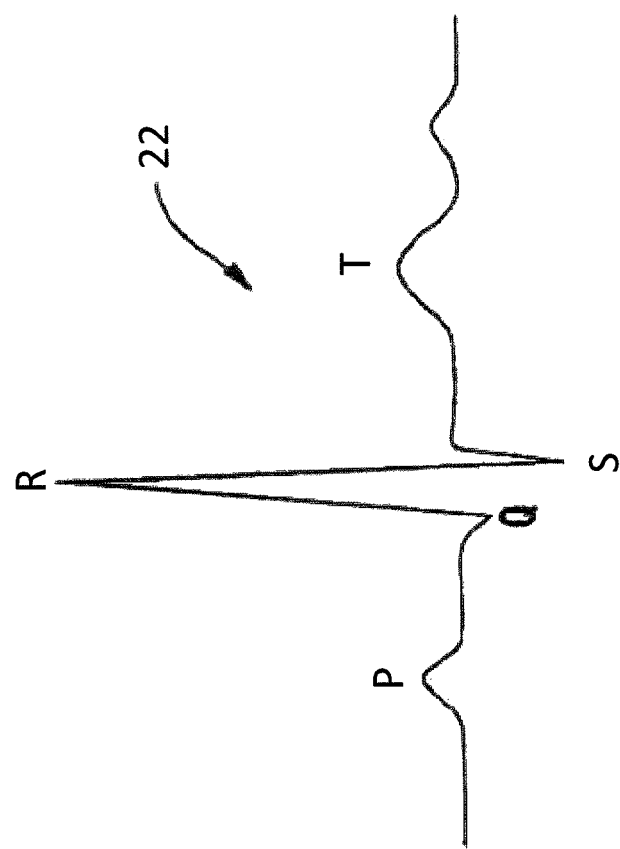
FIG. 4 graphically illustrates an exemplary ECG waveform.

Such electrodes can also be used to detect the electrical activity of the heart over time for electrocardiography (ECG). An ECG is a measurement of the small electrical changes on the skin generated when the heart muscle depolarizes during each heart beat. The output from a pair of electrodes is known as a differential lead. Small rises and falls in the voltage between two electrodes placed on either side of the heart can be processed to produce a graphical ECG representation 22 such as the example ECG shown in FIG. 4. In a typical ECG waveform 22, the ECG waveform includes characteristic regions including the P wave, the QRS complex, the R wave, and the T wave.

In any of the examples described herein, an apparatus may include or be used with an ECG module component 10 and with an electrode assembly configured to sense heart-related signals upon contact with a user's skin, and to convert the sensed heart-related signals to an ECG electric signal. As shown in FIGS. 3A and 3B-3E, a smartphone may include or be used with a case or other apparatus having an ECG module 10 including electrodes 350, 360. As discussed in detail below, the ECG module 10 may transmit (e.g., wirelessly, including by an ultrasonic means) an ECG signal to a smartphone 301. Software on the smartphone 301 can receive and processes the ECG (e.g., wireless signal) in real-time, in addition to SCG data, as described below. The ECG and/or SCG can be further processed to calculate heart rate and identify arrhythmias. The SCG, ECG, heart rate, and rhythm information can be displayed on the smartphone 301, stored locally for later retrieval, and/or transmitted in real-time to a web server via a 2G/3G/4G, WiFi or other Internet connection. In addition to the display and local processing of the SCG and ECG data, the smartphone 301 can transmit, in real-time, the SCG, ECG, heart rate and rhythm data via a secure web connection for viewing, storage and further analysis via a web browser interface (using the 2G/3G/4G or WiFi connectivity of, for example, the smartphone 301). Server software provides for storage, further processing, real-time or retrospective display and formulation of a PDF ECG rhythm strip document and/or other reports and formats for printing remotely or locally.

The ECG module 10 can be configured in any way consistent with its function, i.e., it should include electrodes available to make contact with a user's skin on the hands, chest or other parts of the body, for obtaining the user's ECG, and be configured for transmitting the ECG to a receiving device. For example, a hand-held ECG module 10 can be shaped like a credit card with two electrodes on one surface.

In another configuration, the ECG component 300 is usable as a smartphone protective case 300 as shown in FIGS. 3B-3E. One example configuration utilizes a "slip-on" protective case 300 for an iPhone® or other smartphone 301, the protective case 300 including an integrated ECG electrode assembly 311, 313 and acquisition electronics (not visible). Two or more (e.g., 3 or 4) electrodes may be used to generating leads for collecting ECG data. The ECG electrodes in this example are located on the back of the case 300 opposite of the display screen 309 of the smartphone 301. The smartphone 301, in its ECG-adapted protective case 300, can be placed on a person's chest to generate a modified chest lead. The ECG can be measured by the acquisition electronics and converted into a wireless transmission signal for communicating to the smartphone 301 from the case 300. For example, in some variations the ECG signal is transmitted wirelessly to the smartphone by ultrasound. Thus, the wireless transmission signal may be a frequency modulated ultrasonic signal encoding the ECG signal. Nonlimiting example of suitable carrier or center frequencies include from about 17 kHz to about 40 kHz, or in some embodiments from about 17 kHz to 24 kHz. The frequency modulated ultrasonic signal may be output by a miniature speaker or a piezoelectric buzzer. In some variations the communication between the smartphone and the ECG electrode module sensing the ECG may be two-way (duplex). Further, the methods and apparatuses described herein may synchronize detection of ECG signals with SCG detection, e.g., by initiating detection of SCG upon detection of ECG signals (or vice versa).

Thus, a telecommunications device, such as a smartphone 301, can utilize its built-in components (e.g., microphone, audio codec, and CPU) to acquire, digitize, demodulate, and process SCG and ECG data in real-time. Also, the telecommunications device or smartphone 301 can calculate a real-time heart rate measurement and determine a cardiac rhythm diagnosis like atrial fibrillation, or determine other indicators of cardiac health/fitness (e.g., a modified Tei index). The smartphone 301 can utilize its 2G, 3G, 4G, Bluetooth® and WiFi connectivity to transmit the SCG and/or ECG and other data to a secure web server for real-time distant display, storage and analysis. Also, the SCG and/or ECG data can be stored locally on the smartphone for later review or transmission. SCG and/or ECG data may be processed further and/or stored, and/or displayed, and/or transmitted on using any of the communications capabilities of the telecommunications device. For example, the data may be displayed on the smartphone and/or uploaded into a medical database for storage and/or later review.

In any of the apparatuses and methods described herein, the SCG and/or ECG component may be encrypted for transmission. Any appropriate encryption method may be used, including encryption methods that use keys, such as data encryption standard (DES), advanced encryption standard (AES), and the like. In general any of the systems described herein may encode the data, and an encryption key may be provided so that it can be read and understood by a receiving telecommunications (e.g., phone, tablet, pad, etc.).

Cardiac Functions Determined from the SCG and/or ECG

Figure 2:
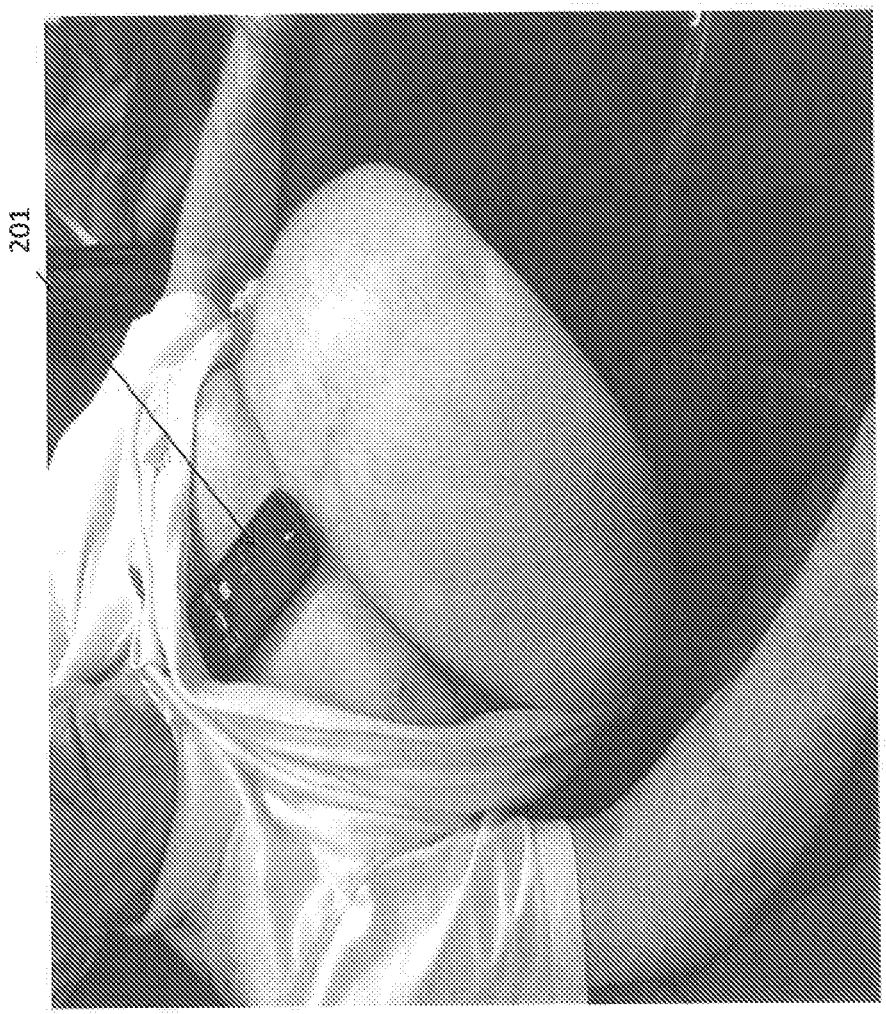
FIG. 2 illustrates a subject/patient using a method and apparatus as described herein and controlling a mobile telecommunications device (in this example, an iPhone™) to detect an SCG and ECG for determining a measure or index of cardiac function.
Figure 3A:
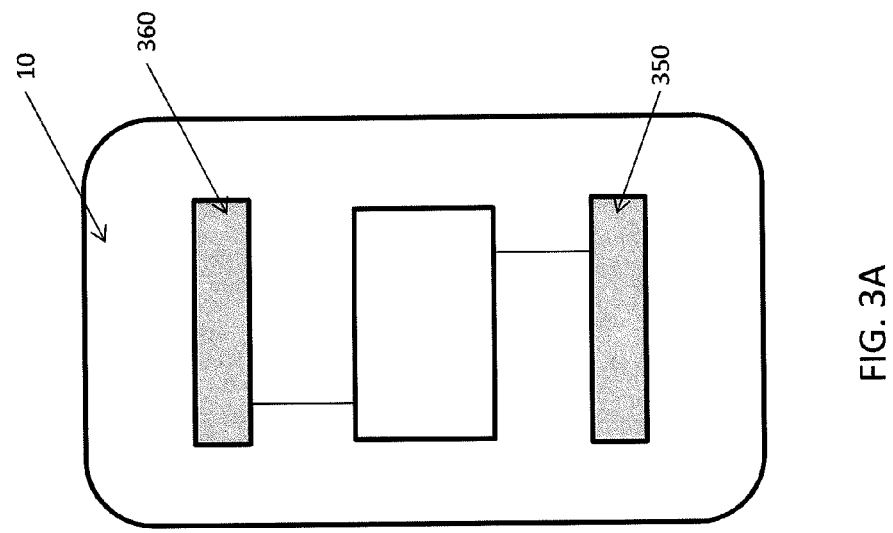
FIG. 3A is a schematic representation of one variation of back of a mobile telecommunications device (e.g., smartphone) including a module having sensors for measuring ECG (e.g., electrodes).
Figure 5:
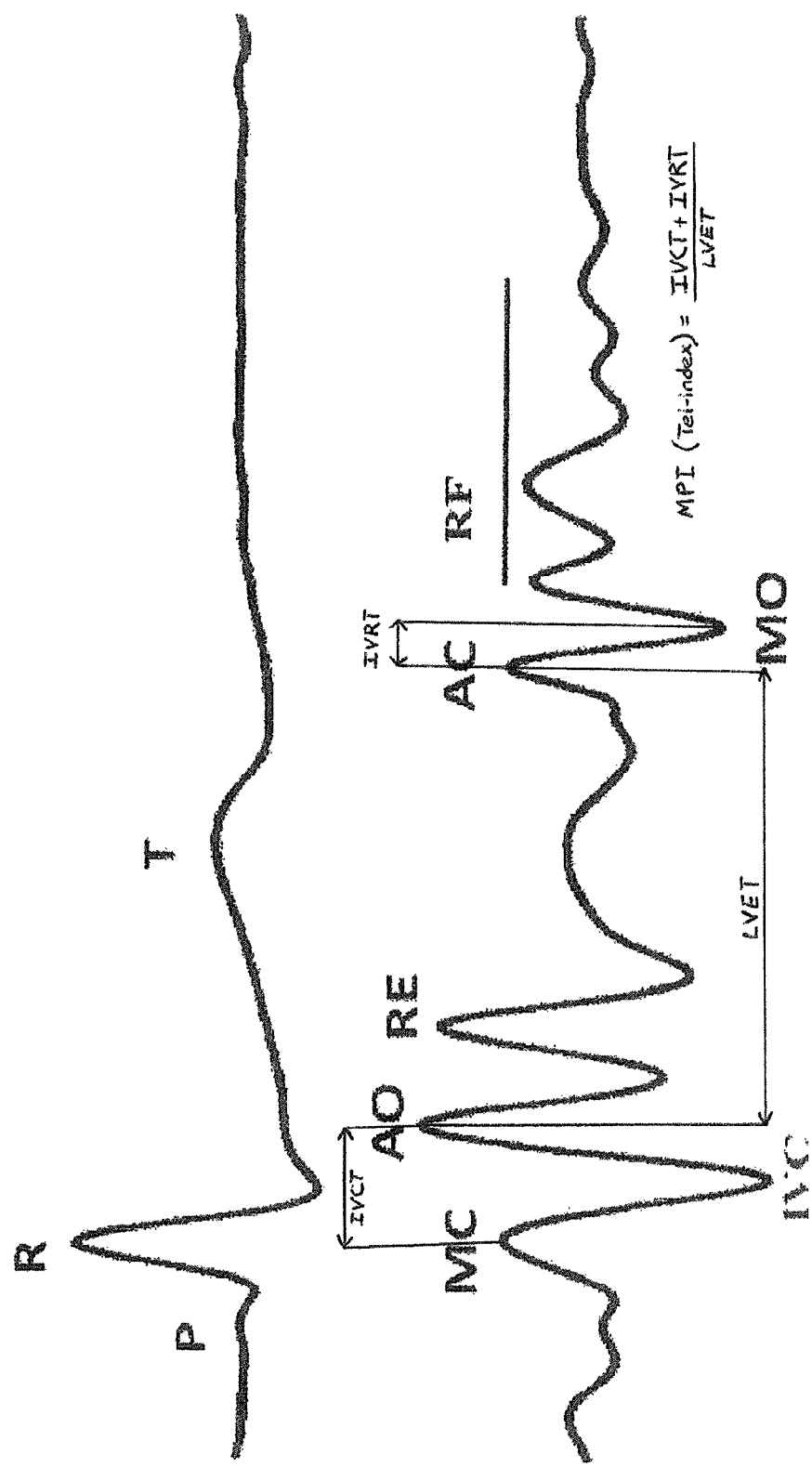
FIG. 5 illustrates a pair of synchronized ECG and SCG waveforms (for a single ECG and SCG cycle).

A number of cardiac events, indices, and data can be derived from the SCG and/or ECG, including systolic and diastolic parameters for left ventricle performance. FIG. 5 illustrates a side-by-side synchronized ECG and SCG waveform with annotations showing characteristics corresponding to specific points on the SCG and ECG curves. Further, FIG. 6 illustrates an annotated SCG taken using a mobile telecommunications device 201 (iPhone™) on a subject as shown in FIG. 2.

In some variations the apparatus for determining an indicator of cardiac performance includes control logic to process SCG and/or ECG data. The apparatus may also be configured to both record and to analyze the SCG and/or ECG. For example, the apparatus (including control logic/an instruction set) may be configured to determine characteristic parameters from the SCG as described herein.

For example, the upper trace in FIG. 5 corresponds to an ECG trace; the lower trace is an SCG waveform (a single cycle) synchronized with the ECG trace. In FIG. 5, characteristic regions of the SCG reflect the time of mitral valve closure (MC), isovolumetric contraction (IVC), aortic valve opening (AO), rapid ejection (RE), aortic valve closure (AC), mitral valve opening (MO), and rapid filling (RF). In this example, the peaks and/or troughs of the waveforms are taken to represent the approximate time of each event, as labeled. A pre-ejection period (PEP) and left ventricle ejection time (LVET or ET) can be determined from points on the ECG and the SCG curves.

Figure 6:
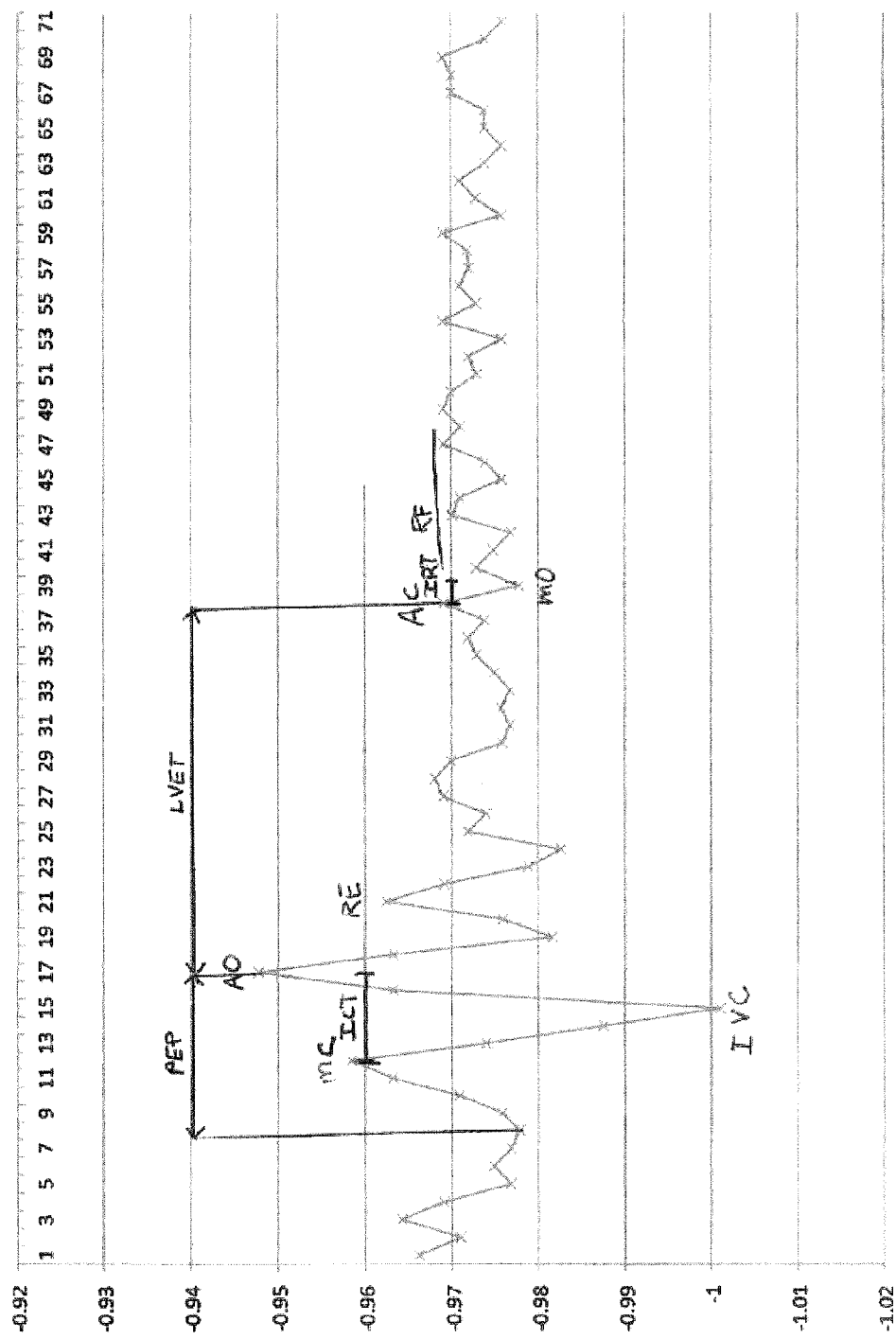
FIG. 6 is an example of an SCG taken using a smartphone.

An SCG such as the one shown in FIGS. 5 and 6 can be used to determine approximate timing of cardiac events. For example, left ventricle ejection time (ET or LVET) can be calculated by determining the time from the aortic valve opening (AO) and the aortic valve closure (AC). The isovolumetric contraction time (ICT) can be calculated by determining the time between the mitral valve closure (MC) and the aortic valve opening (AO). The isovolumetric relaxation time (IRT) can be calculated by determining the time between the aortic valve closure (AC) and the mitral valve opening (MO). Similarly, a pre-ejection period (PEP) can be calculated by determining the time between the Q wave on the ECG and aortic valve opening (AO) on the ECG. A contractility coefficient can be calculated as PEP/LVET. The left ventricular filling time can be calculated by determining the time between the mitral valve opening and the mitral valve closure (MO-MC). The rapid ventricular filling time can be calculated by determining the time between the mitral valve opening (MO) and the rapid filling (RF).

Thus, the SCG alone gives a large number of cardiac characteristics that may be used to estimate cardiac fitness; in combination with the ECG, additional characteristics may be determined. Further the ECG, when synchronized with the SCG, may be used to help identify characteristics on the SCG, and may be used to help identify individual SCG cycles. For example, the R-wave of the ECG may correspond to the MC in the SCG.

Thus, a mobile telecommunications device having an accelerometer may be used to detect an SCG by placing the mobile device 201 on the subject's chest when the subject is lying supine, as shown in FIG. 2. The mobile telecommunications device may confirm subject compliance (e.g., that the device is properly positioned) using the device's gyroscope and/or accelerometer. In some variations the method may also include concurrently (or over the same time period) measuring ECG, for example, with electrodes in a case in which the mobile telecommunications device is residing. These methods may be performed by a cardiac performance monitoring system.

When taking the SCG (and/or ECG) signals may be recorded for a predetermined (or variable/situation dependent) period of time, and signals averaged over that time period. For example, a composite/average/filtered SCG signal and/or ECG signal may be determined from a window of measurement time (e.g., 10 second, 20 second, 30 seconds, 40 seconds, 50 second, 1 minute, 2 minutes, 3 minutes, 4 minutes, 5 minutes, etc.). The resulting SCG signal may be referred to as a processed SCG signal. The processed SCG (and in some variations ECG signal) may then be used to determine other parameters, as mentioned above. As mentioned, the ECG R-wave peak may be used as a fiduciary for alignment of the ECG and/or SCG complexes (cycles) for signal averaging which retains repeatable feature but may reduce noise.

In some variations, the cardiac performance monitoring system may then analyze the SCG and/or ECG to determine one or more parameter of cardiac performance. For example, the cardiac performance monitoring system may be configured to determine one or more index of cardiac function (index of cardiac fitness). The parameters, including the index, may be displayed, stored, and/or uploaded to a remote site for patient monitoring by a physician.

For example, in some variations, the cardiac performance monitoring system is configured to calculate a modified Tei index from the SCG.

Calculation of Modified Tei Index

The Tei index is typically calculated using pulsed Doppler ultrasound to obtain the cardiac event timing, e.g., using averages over three or more cardiac cycles. More recently, ultrasonic tissue Doppler Imaging (TDI) has been used to measure a beat-by-beat "modified Tei Index." Described herein are methods to calculate a modified Tei index using an SCG.

FIGS. 5 and 6 illustrate the use of SCG (alone or in conjunction with an ECG) to calculate a modified Tei index. The modified Tei index can be calculated based on the isovolumetric relaxation time (IVRT or IRT), isovolumetric contraction time (IVCT or ICT), and left ventricular ejection time (LVET or ET). The IRT, ICT, and ET can be derived or calculated based on the SCG alone or in combination with a synchronized ECG. For example, time corresponding to the peak of the R wave can be used with landmarks from the SCG to calculate the isovolumetric relaxation time (IRT), isovolumetric contraction time (ICT), and ejection time (ET).

Specifically, a formula for calculating the modified Tei index is equal to the sum of the isovolumetric contraction time (ICT) and the isovolumetric relaxation time (IRT) divided by the ejection time: (ICT+IRT)/ET.

Another way to represent the Tei index is by the formula (a−b)/b where a is the interval between cessation and onset of the mitral inflow and b is the ejection time (ET). The ejection time corresponds to the ejection time of the left ventricular outflow. The IRT can be measured by subtracting the interval between the R wave and the cessation of the left ventricle (LV) outflow from the interval between the R wave and the onset of mitral inflow.

In some embodiments the modified Tei index and other cardiac functions can be derived or estimated from just the SCG. The cardiac performance monitoring apparatus described herein may include logic for calculating this index (e.g., modified Tei index determination logic) that may operate on the processor of the mobile telecommunications device using the SCG and in some variations the synchronized ECG signals.

The systems and methods described herein can therefore allow measurement of the modified Tie-index (and/or other cardiac fitness measures) on a beat-to-beat basis or an averaged basis. The patient may perform these measurements at home, and could track them daily, hourly, etc. (multiple times per day), or over many days (days, weeks, months, years). The data may be saved locally (e.g. on the smartphone) and/or uploaded to a database or transmitted to a medical provided or monitoring service.

FIG. 2 and FIG. 6 illustrate the use of an apparatus as described herein to detect SCG and calculate an indicator of cardiac fitness. In this example, as shown in FIG. 2, the patient records SCG data from the smartphone placed on the chest. FIG. 6 illustrates one variation of the resulting SCG raw trace. In FIG. 6, the trace, taken from the accelerometer of the smartphone, has been marked to indicate characteristic waveforms. This trace has not been filtered or smoothed, which may result in a more regular an easily read SCG waveform. In FIG. 6 the LVET, ICT and IRT have been marked, based on the determination of which peaks correspond to MC, AO, AC and MO. Additional characteristics have also been marked. In FIG. 6, the modified Tei index may be calculated based on the values of ICT, IRT and LVET (e.g., (ICT+IRT)/LVET). FIG. 6 is a single cycle of an SCG; additional SCG cycles may be analyzed and averaged.

Methods for using the mobile telecommunication devices Prior art methods use large accelerometer to take the SCG. These devices are only practical in the context of commercial medical facilities, for example see the testing setup shown in FIG. 1. The devices and methods disclosed herein allow for the use of a handheld device, such as a mobile telecommunications device to take the SCG as illustrated in FIG. 2. The use of a compact and commonly available mobile telecommunication device allows for the user to take the SCG at home instead of at a commercial medical facility.

The cardiac performance monitoring system described herein can use a telecommunications device at home by the user to measure the SCG and/or ECG. The user can place the telecommunications device on their chest. The device is preferably in contact with the skin of the user's chest. The device can be placed near the bottom of the sternum of the user. This positioning works with the male and female anatomy.

Figure 7:
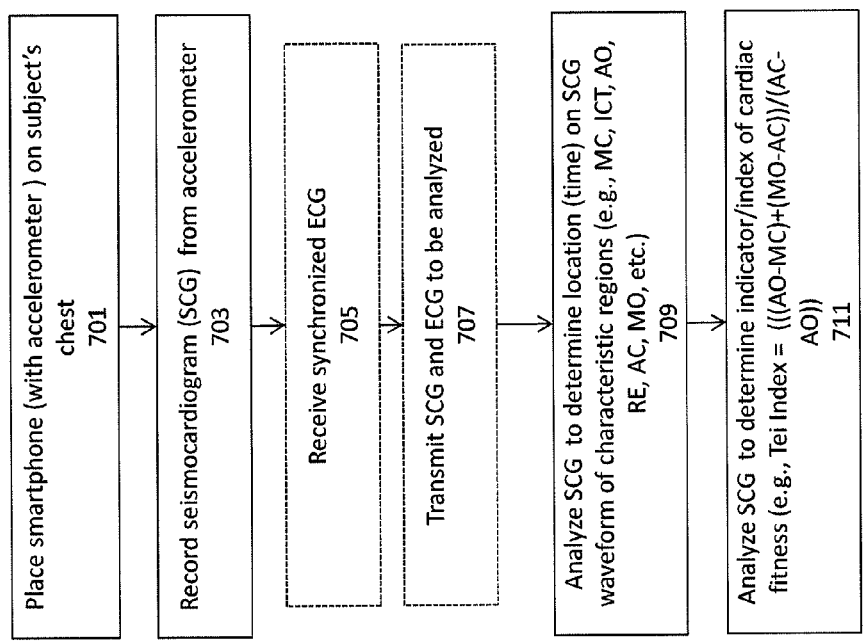
FIG. 7 is an exemplary chart illustrating steps that may be performed as described herein.

FIG. 7 illustrates one method (and some of the control logic) for the operation of the apparatus as described herein, in one variation. In FIG. 7, the user can place the device on their chest 701 while lying down in a supine position. The user is preferably resting during the testing. Typically 30 seconds of data is sufficient. In some cases the data can be collected for about 10 seconds or less, about 20 seconds or less, about 30 seconds or less, or about 60 seconds or less. In some cases a single heartbeat can be sufficient for taking the SCG and ECG. The apparatus records a seismocardiogram during the time period 703; in some variations an ECG may also be recorded during this same period of time, and the synchronized ECG received by the apparatus 705. The SCG (and in some variations ECG data) may then be analyzed either on the smartphone apparatus or (optionally) after transfer to another processor 707. The SCG (and in some cases the ECG) may then be analyzed to determine the location (e.g., the times during the SCG cycle) on SCG waveform of characteristic regions (e.g., MC, ICT, AO, RE, AC, MO, etc.) 709. These characteristic times can then be used to determine one or more indicator or index of cardiac fitness (e.g., ventricular performance and filling, Tei index, etc.) 711. Additional and alternative steps are also described herein, including displaying, storing and transmitting the SCG and/or ECG and data extracted from the SCG and/or ECG.

The telecommunications device can include a gyroscope that can be used to verify the orientation of the device during testing to verify that the patient is in a supine position.

Previously it was only practical to measure the cardiac functions when the patient was at the hospital or doctor's office. The convenience of at home measurement allows for more frequent measurements and tracking of the cardiac functions. More frequent measurements allows for tracking the changes and trends of the user's cardiac functions. Tracking the user's cardiac function over time allows for the determination of a baseline for the user's cardiac function. The user's own baseline can be used as a control value. The cardiac function data that is subsequently measured can be compared to the user's baseline or control value.

Variations in cardiac function can be tracked over time. If the variation from the baseline or control value exceeds a certain amount or threshold then the user can be given a warning. The warning and data can be sent to the user's doctor or nurse as well. The warning notification can be sent out for variations of about 10%, 20%, 30%, 40%, 50%, 60%, 70%, 80%, 90%, or 100% from the baseline. For example, sudden increases in the Tei index can be indicative of heart failure or imminent heart problems.

The measure of the user's cardiac function can vary throughout the day, for example between morning, afternoon, and evening measurements. The user can be instructed to take the measurements at a certain time of the day or the data can be adjusted based on the typical variability between measurements taken during the morning, afternoon, and evening.

The user can be instructed to take measurements multiple times a day, once a day, once a week, or at other time intervals, and can be notified by phone call, email, SMS message, etc.

In some embodiments the data taken by the telecommunications device can be presented to the user in numerical or graphical form. In some embodiments the data taken by the telecommunications device can be uploaded to a remote server. The data can later be accessed or presented to a medical professional in numerical or graphical form.

In some embodiments the SCG can be taken by itself without taking a concurrent ECG. The SCG by itself can be used to estimate the cardiac functions. In some embodiments, the SCG data can be analyzed with the assumption of a typical ECG response for the patient. In one example the ECG and SCG could be taken at a medical facility and calibrated using the Doppler ultrasound or TDI measurements. The patient could then use the mobile telecommunications device to measure the SCG and the software could correlate the SCG data with the ultrasonically-derived SCG results to arrive at a representation of the cardiac function of the user.

In some embodiments the methods disclosed herein can be used to take an SCG and/or ECG of the patient by a doctor, nurse, or other medical professional.

Smartphone Application and Software

The present application discloses a smartphone application that can be used to perform any of the methods, logic, calculations, and analysis disclosed herein. Thus, the cardiac performance monitoring system may include this application. This application (program, executable code, logic, etc.) is typically stored in a non-transient medium; thus may include any non-transitory computer-readable storage medium storing a set of such instructions capable of being executed, e.g., by a smartphone.

The smartphone application includes instructions for the telecommunications device to use an accelerometer to measure vibrations.

The smartphone application can include instructions for the telecommunications device to communicate wirelessly with the ECG component. The wireless communication can include communication by ultrasonic signals. The ultrasonic signals can be encoded with digital or analog data corresponding to the ECG reading.

The smartphone application includes instructions for the telecommunications device to simultaneously collect ECG and SCG data. The ECG and SCG data can be time-synced based on the time clock of the telecommunications device.

The smartphone application can include instructions to average the ECG and SCG data collected during the analyzed time interval.

Any of the data analysis disclosed herein can be performed by the logic or microprocessor contained on the telecommunications device. Any of the data analysis disclosed herein can also be performed by a remote server. Any of the data analysis can be performed by a combination of both the telecommunications device and the remote server.

The smartphone application can include instructions for analyzing the ECG and SCG data to determine any of the peaks, points, or times of interest described herein.

The smartphone application can include instructions for the telecommunications device to transmit data collected to a remote server. Any data collected by the telecommunications device can be uploaded and analyzed by a remote server.

The smartphone application can include instructions to analyze the collected data to establish a baseline or control or the patient. The application can include trend monitoring to track changes in the cardiac function.

The smartphone application can send reminders to the patient to conduct tests. The reminder can be sent via text message, e-mail, calendar reminders, phone notifications, or other methods. The reminder can be sent based on the desired frequency of testing, for example, daily, weekly, or multiples times per day.

The smartphone application can analyze GPS and gyroscope data collected by the telecommunications device while measuring the SCG to determine the location and orientation of the device during measuring. The application can provide a notification or error message if the gyroscope indicates that the phone is incorrectly placed or if the patient is not in a supine or reclined position.

The smartphone application can include instructions to communicate remotely with a remote server or the internet. The application can also allow for remote monitoring by a medical professional.

The smartphone application can include instructions to notify the user or a medical professional if the variations from the baseline or control value exceed a certain amount or threshold. The warning and data can be sent to the user's doctor or nurse. The warning notification can be sent out for variations of about 10%, 20%, 30%, 40%, 50%, 60%, 70%, 80%, 90%, or 100% from the baseline.

The cardiac performance monitoring systems described herein may also be configured to determine one or more of cardiac rhythm (including detection of NSR or AF), and/or heart rate, and/or heart rate variability. For example, SCG may be used to determine heart rate (or heart rate variability). The SCG may also be used to detect respiration and the respiratory cycle components (e.g., by examining the low-frequency components) and respiratory rate.

In some variations, the cardiac performance monitoring system may also include a "paced breathing" module to guide a patient through the appropriate paced breathing session while the smartphone is in contact and measuring SCG and/or ECG, from which heart rate variability (HRV) could be determined. This may allow monitoring of the status of their heart failure by evaluating the sympathetic-parasympathetic balance of their autonomic nervous system. Decreased HRV is an early warning of CHF decompensation.

Additional Applications

The concepts disclosed in the present application are applicable to any application where monitoring cardiac health and function over time is desirable. The convenience of using the testing methods disclosed herein for at-home testing allows for the patient to develop a baseline value to represent their cardiac health. The cardiac health can be monitored over time to look for any changes in the cardiac health of the patient.

The methods can be used by heart transplant patients to monitor their cardiac health after receiving a transplant. A significant change in the cardiac function can be indicative of the body rejecting the transplanted organ. Early detection of potential problems with the transplanted organ can signal the need for early treatment or diagnosis and possibly prevent a fatal event.

Some drug treatments can cause complications with the heart function in a patient. The ability to monitor the overall cardiac function and loading status can be useful to determine when and if the drug treatment causes any adverse effects on the cardiac function of the patient. For example, some chemotherapy medications can be toxic to the heart. The methods disclosed herein can be used to watch for any decreases in the cardiac function of the patient. If a statistically significant decrease in the cardiac function is observed then the dosage of the medication can be decreased or another medication could be substituted.

The telecommunications devices with the accelerometer can be used to measure trembling or shaking in the patient. For example, the devices can be used to measure shaking in patients having Parkinson's disease.

The respiratory rate of the user can be determined using the telecommunications device and accelerometer. The vibrations on the user's chest can indicate the breathing rate in addition to the heartbeat. The measured vibrations can be analyzed to detect the peaks in the signal and apply a low pass filter to remove some of the data corresponding to the heartbeat. The data can then be analyzed to extract data on the respiratory rate of the user.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A non-transitory computer-readable storage medium storing a set of instructions capable of being executed by a smartphone having an accelerometer, that, when executed by the smartphone, causes the smartphone to record a seismocardiogram (SCG) from the smartphone's accelerometer by detecting vibrations on a patient's chest corresponding to heart motion for a first time period, further wherein the set of instructions, when executed by the smartphone, cause the smartphone to do at least one of: analyze the SCG to determine an index of cardiac function, display the SCG, transmit the SCG, or store the SCG, wherein the set of instructions, when executed by the smartphone, causes the smartphone to analyze the SCG to determine the index of cardiac function by taking a ratio of the sum of isovolumetric contraction time (ICT) and isovolumetric relaxation time (IRT) divided by the left ventricle ejection time (ET).

2. The non-transitory computer-readable storage medium of claim 1, further wherein the set of instructions, when executed by the smartphone, causes the smartphone to receive an electrocardiogram (ECG) from the patient, wherein the ECG is taken over the first time period.

3. The non-transitory computer-readable storage medium of claim 1, wherein the set of instructions, when executed by the smartphone, causes the smartphone to identify two or more characteristic regions of the SCG from the regions consisting of: mitral valve closure, isovolumetric contraction, aortic valve opening, rapid ejection, aortic valve closure, mitral valve opening, and rapid filling.

4. The non-transitory computer-readable storage medium of claim 3, wherein the set of instructions, when executed by the smartphone, causes the smartphone to identify two or more characteristic regions of the SCG using an electrocardiogram (ECG) that is taken over the first time period.

5. The non-transitory computer-readable storage medium of claim 1, wherein the set of instructions, when executed by the smartphone, causes the smartphone to instruct the patient to position the smartphone against the patient's chest prior to recording the SCG.

6. The non-transitory computer-readable storage medium of claim 1, wherein the set of instructions, when executed by the smartphone, causes the smartphone to verify the orientation of the smartphone and notify the user if the orientation of the smartphone during the first time period was incorrect.

7. The non-transitory computer-readable storage medium of claim 1, wherein the set of instructions, when executed by the smartphone, causes the smartphone to identify multiple SCG cycles taken during first time period and to average the multiple SCG cycles.

8. The non-transitory computer-readable storage medium of claim 1, wherein the set of instructions, when executed by the smartphone, causes the smartphone to identify multiple SCG cycles using an electrocardiogram (ECG) that was taken over the first time period.

9. A non-transitory computer-readable storage medium storing a set of instructions capable of being executed by a smartphone having an accelerometer, that, when executed by the smartphone, causes the smartphone to: record a seismocardiogram (SCG) from the smartphone's accelerometer by detecting vibrations on a patient's chest corresponding to heart motion for a first time period; and receive an electrocardiogram (ECG) from the patient over the first time period; analyze the SCG to determine an index of cardiac function for the patient; and do at least one of: display, transmit and store the index of cardiac function, wherein the set of instructions, when executed by the smartphone, causes the smartphone to analyze the SCG to determine an index of cardiac function for the patient by taking a ratio of the sum of isovolumetric contraction time (ICT) and isovolumetric relaxation time (IRT) divided by the left ventricle ejection time (ET).

10. The non-transitory computer-readable storage medium of claim 9, wherein the set of instructions, when executed by the smartphone, causes the smartphone to analyze the SCG to determine an index of cardiac function for the patient by identifying characteristic regions of the SCG using the ECG.

11. The non-transitory computer-readable storage medium of claim 9, wherein the set of instructions, when executed by the smartphone, causes the smartphone to analyze the SCG to determine an index of cardiac function for the patient by identifying two or more of mitral valve closure, isovolumetric contraction, aortic valve opening, rapid ejection, aortic valve closure, mitral valve opening, and rapid filling.

12. The non-transitory computer-readable storage medium of claim 9, wherein the set of instructions, when executed by the smartphone, causes the smartphone to identify multiple SCG cycles using an ECG that was taken over the first time period and to average the multiple SCG cycles.

13. The non-transitory computer-readable storage medium of claim 9, wherein the set of instructions, when executed by the smartphone, causes the smartphone to verify the orientation of the smartphone and notify the user if the orientation of the smartphone during the first time period was incorrect.

14. A method of determining an index of cardiac function for a patient using a smartphone having an accelerometer, the method comprising: placing the smartphone on the patient's chest; recording a seismocardiogram (SCG) for a first time period using the smartphone's accelerometer; and analyzing the SCG to determine an index of cardiac function, wherein analyzing the SCG to determine an index of cardiac function comprises analyzing the SCG using the smartphone to determine the index of cardiac function by taking a ratio of the sum of isovolumetric contraction time (ICT) and isovolumetric relaxation time (IRT) divided by the left ventricle ejection time (ET).

15. The method of claim 14, further comprising receiving an electrocardiogram (ECG) in the smartphone, wherein the ECG is recorded from the patient over the first time period.

16. The method of claim 14, wherein placing the smartphone on the patient's chest comprises the patient placing the smartphone on the patient's own chest.

17. The method of claim 14, further comprising using the smartphone to verify the orientation of the smartphone on the patient's chest before or during the first time period.

18. The method of claim 14, wherein analyzing the SCG to determine an index of cardiac function comprises identifying multiple SCG cycles taken during first time period and averaging the multiple SCG cycles.

19. The method of claim 14, wherein analyzing the SCG to determine an index of cardiac function comprises identifying multiple SCG cycles taken during the first time period using an electrocardiogram (ECG) that was recorded from the patient over the first time period.

20. The method of claim 14, wherein analyzing the SCG to determine an index of cardiac function comprises identifying two or more characteristic regions of the SCG from the regions consisting of: mitral valve closure, isovolumetric contraction, aortic valve opening, rapid ejection, aortic valve closure, mitral valve opening, and rapid filling.

21. The method of claim 14, further comprising displaying the SCG on the smartphone.

22. The method of claim 14, further comprising transmitting the SCG to a remote server using the smartphone.

23. A method of determining an index of cardiac function for a patient using a smartphone having an accelerometer, the method comprising: placing the smartphone on the patient's chest; recording a seismocardiogram (SCG) for a first time period using the smartphone's accelerometer; receiving an electrocardiogram (ECG) in the smartphone, wherein the ECG is recorded from the patient over the first time period; and analyzing the SCG to determine an index of cardiac function, wherein analyzing the SCG to determine an index of cardiac function comprises analyzing the SCG using the smartphone to determine the index of cardiac function by taking a ratio of the sum of isovolumetric contraction time (ICT) and isovolumetric relaxation time (IRT) divided by the left ventricle ejection time (ET).

24. The method of claim 23, further comprising using the smartphone to verify the orientation of the smartphone on the patient's chest before or during the first time period.

25. The method of claim 23, wherein analyzing the SCG to determine an index of cardiac function comprises identifying multiple SCG cycles taken during the first time period using the ECG.

26. The method of claim 23, further comprising transmitting the SCG to a remote server using the smartphone.

* * * * *